(12) United States Patent
Tebbutt et al.

(10) Patent No.: US 9,155,855 B2
(45) Date of Patent: Oct. 13, 2015

(54) MOUTHPIECE

(75) Inventors: Adam Alexander Tebbutt, Auckland (NZ); Blair Albert Neal, Victoria (SC); Lewis George Gradon, Auckland (NZ); Alastair Edwin McAuley, Auckland (NZ); Mark Joseph Haycock, Oxford (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1036 days.

(21) Appl. No.: 10/538,239

(22) PCT Filed: Dec. 5, 2003

(86) PCT No.: PCT/NZ03/00269
§ 371 (c)(1),
(2), (4) Date: Jan. 3, 2006

(87) PCT Pub. No.: WO2004/052438
PCT Pub. Date: Jun. 24, 2004

(65) Prior Publication Data
US 2006/0112962 A1    Jun. 1, 2006

(30) Foreign Application Priority Data

Dec. 6, 2002 (NZ) .................................. 523020
Mar. 26, 2003 (NZ) .................................. 524982
Sep. 12, 2003 (NZ) .................................. 528222
Oct. 2, 2003 (NZ) .................................. 528646

(51) Int. Cl.
*A61M 16/04* (2006.01)
*A61M 16/06* (2006.01)
*A61M 16/08* (2006.01)

(52) U.S. Cl.
CPC ....... *A61M 16/0488* (2013.01); *A61M 16/0493* (2014.02); *A61M 16/06* (2013.01); *A61M 16/0616* (2014.02); *A61M 16/08* (2013.01)

(58) Field of Classification Search
CPC .... A62B 9/06; A61M 16/06; A61M 16/0488; A61M 16/049; A61M 16/0493; A61M 16/0495; A61M 16/0616

USPC .......... 128/206.28, 206.29, 207.18, 848, 859, 128/861, 201.26, 201.18, 204.18, 205.25, 128/206.21, 200.26, 860
See application file for complete search history.

(56) References Cited

U.S. PATENT DOCUMENTS 443,191 A * 12/1890 Illing ....................... 128/203.22
690,663 A    1/1902 Pratt
(Continued)

FOREIGN PATENT DOCUMENTS

DE    19944242    3/2001
EP     818213    7/1997
(Continued)

OTHER PUBLICATIONS

United States Patent Application Publication No. 2002/0069872; Inventor: Gradon et al.; Published on Jun. 13, 2002; Entitled: Mouthpiece.

*Primary Examiner* — Justine Yu
*Assistant Examiner* — LaToya M Louis
(74) *Attorney, Agent, or Firm* — Knobbe, Martens, Olson & Bear, LLP.

(57) ABSTRACT

Mouthpiece (1) having vestibular shield (21) overlapping a user's teeth and gums, gases passageway means extending through said vestibular shield allowing for the passage of said gases through mouthpiece and extra oral sealing (25) means associated with gases passageway, said passageway in use causes gases to be diffused (outlets 23, 24) when exiting from gases passageway. Mouth piece may have a noseflap to seal the user's nose or provide a passageway for user's nasal passages. Mouthpiece may have adjustment means to alter distance between said vestibular shield and said extra-oral sealing means.

24 Claims, 26 Drawing Sheets

(56) References Cited

U.S. PATENT DOCUMENTS

| | | | | |
|---|---|---|---|---|
| 718,785 | A * | 1/1903 | McNary | 128/207.18 |
| 1,362,766 | A * | 12/1920 | McGargill | 128/205.27 |
| 1,445,010 | A * | 2/1923 | Feinberg | 128/207.18 |
| 1,592,345 | A * | 7/1926 | Drager | 128/207.17 |
| 1,978,994 | A * | 10/1934 | Fortunato | 128/201.16 |
| 2,521,084 | A * | 9/1950 | Oberto | 128/206.29 |
| 3,291,121 | A * | 12/1966 | Vizneau | 128/205.15 |
| 3,508,543 | A * | 4/1970 | Aulicono | 128/202.28 |
| 3,658,058 | A * | 4/1972 | Neidhart et al. | 128/201.18 |
| 3,860,042 | A * | 1/1975 | Green | 128/201.11 |
| 4,098,270 | A | 7/1978 | Dolby | |
| 4,440,165 | A * | 4/1984 | Holzel | 128/205.28 |
| 4,470,413 | A | 9/1984 | Warncke | |
| 4,495,945 | A | 1/1985 | Liegner | |
| 4,573,463 | A * | 3/1986 | Hall | 128/205.24 |
| 4,862,909 | A | 9/1989 | Kim | |
| 4,895,143 | A * | 1/1990 | Fisher | 128/206.29 |
| 5,005,571 | A * | 4/1991 | Dietz | 128/207.18 |
| 5,537,994 | A * | 7/1996 | Thornton | 128/204.18 |
| 5,560,354 | A * | 10/1996 | Berthon-Jones et al. | 128/205.25 |
| 5,590,643 | A | 1/1997 | Flam | |
| 5,752,510 | A * | 5/1998 | Goldstein | 128/207.18 |
| 5,954,048 | A * | 9/1999 | Thornton | 128/201.18 |
| 5,983,892 | A * | 11/1999 | Thornton | 128/201.26 |
| 6,012,455 | A * | 1/2000 | Goldstein | 128/207.18 |
| 6,112,746 | A * | 9/2000 | Kwok et al. | 128/207.13 |
| 6,209,542 | B1 * | 4/2001 | Thornton | 128/206.29 |
| 6,405,729 | B1 * | 6/2002 | Thornton | 128/206.29 |
| 6,571,798 | B1 * | 6/2003 | Thornton | 128/206.21 |
| 6,679,257 | B1 * | 1/2004 | Robertson et al. | 128/204.18 |
| 6,820,741 | B2 | 11/2004 | Ferguson et al. | |
| 7,658,189 | B2 * | 2/2010 | Davidson et al. | 128/205.25 |
| 7,708,017 | B2 * | 5/2010 | Davidson et al. | 128/206.24 |
| 2001/0029954 | A1 * | 10/2001 | Palmer | 128/207.17 |
| 2002/0043265 | A1 * | 4/2002 | Barnett et al. | 128/206.24 |
| 2002/0069872 | A1 | 6/2002 | Gradon et al. | |
| 2002/0104541 | A1 * | 8/2002 | Bibi et al. | 128/205.25 |
| 2003/0015198 | A1 * | 1/2003 | Heeke et al. | 128/204.18 |
| 2003/0089371 | A1 * | 5/2003 | Robertson et al. | 128/201.26 |
| 2003/0196662 | A1 * | 10/2003 | Ging et al. | 128/204.15 |
| 2004/0211430 | A1 * | 10/2004 | Pivovarov | 128/848 |
| 2005/0022821 | A1 * | 2/2005 | Jeppesen | 128/848 |
| 2006/0112962 | A1 * | 6/2006 | Tebbutt et al. | 128/206.29 |
| 2006/0207597 | A1 * | 9/2006 | Wright | 128/206.11 |
| 2006/0283461 | A1 * | 12/2006 | Lubke et al. | 128/207.11 |
| 2008/0006270 | A1 * | 1/2008 | Gershman et al. | 128/203.28 |

FOREIGN PATENT DOCUMENTS

| | | | |
|---|---|---|---|
| EP | 845277 | A2 * | 6/1998 |
| EP | 1075848 | | 7/2000 |
| EP | 1075848 | A2 * | 2/2001 |
| GB | 2 277 688 | | 11/1994 |
| WO | WO 90/03199 | | 4/1990 |
| WO | WO 95/14507 | | 6/1995 |
| WO | WO 99/58181 | | 11/1999 |

* cited by examiner

MOUTHPIECE

BACKGROUND OF THE INVENTION

1. Field of Invention

This invention relates to a system for oral delivery of gases pressurized above ambient, and in particular, to a system, including a novel mouthpiece, for the oral delivery of air or gases in continuous positive airway pressure (CPAP) treatments of sleeping disorders such as sleep apnoea.

2. Description of the Prior Art

Sleep apnoea treatments have been significantly advanced with the introduction of continuous positive airway pressure (CPAP) treatments. These treatments, as introduced, involve the supply of gases from a gases supply or blower to a patient or user through a conduit and nasal mask to provide an elevated internal pressure in the user's airways to assist the muscles to keep the airways open. This air stream is provided to the user through a nasal mask applied over the nose and held in place by a harness. This configuration has been almost universally adopted based on the well-known observation that humans show a decided preference for nasal breathing during sleep. For this reason, little development has been undertaken into other possible methods of providing the pressurized air stream to a user.

Oral delivery is suggested in EP818213, which shows an apparatus for oral delivery of air in a CPAP treatment. The apparatus includes a mouthpiece adapted to fit inside the mouth between the roof of the mouth, the hard palate, and the tongue, and having a periphery that can be gripped between the teeth. It is thought by the applicants that this is significantly more intrusive than is necessary and is liable to movement and consequent discomfort (although not outright removal) under the relaxation of sleep. It has the additional disadvantage that with the user fully relaxed, such as in the case of sleep, distension in the user's jaw and subsequent opening of the mouth can reduce the sealing effectiveness of the mouthpiece and reduce the efficacy of the CPAP treatment.

The mouthpiece in EP818213 is gripped between the user's teeth; thus a further disadvantage results in that the mouthpiece requires custom orthodontic fitting to ensure that the mouthpiece matches the user's mouth and teeth layout. Custom orthodontic fitting is time consuming and removes the capability of effective mass manufacture. Consequently, the mouthpiece in EP818213 is expensive, creating a significant barrier to the adoption of the device by the user.

A similar gases delivery mouthpiece, for use with a respirator, is shown in WO90/03199. WO90/03199 discloses an orthodontic device that is adapted to be gripped between the jaws of a user and to accommodate the user's teeth within a series of upper and lower cavities. A base member of the mouthpiece is shaped and fits against the hard palate of the user. This mouthpiece again has the disadvantage of requiring custom orthodontic fitting. Furthermore, as a result of the mouthpiece's substantial thickness and size, the mouthpiece is substantially rigid in the vestibule regions of the mouth. The mouthpiece is clamped in place by an outer shield that engages the outside of the user's lips.

A paper by E Veres entitled "Clinical trial of an oral vestibular shield for the control of snoring" (Journal of the Dental Association of South Africa, January 1993) describes the use of a shield intended to be retained in the vestibule of the mouth to seal the mouth and to promote nasal breathing which has been conventionally considered to be more beneficial than oral breathing. Humidified CPAP treatments delivered orally, however, actually derive greater benefit than those delivered nasally because secondary leakage through the nasal passages during oral delivery is significantly less than oral leakage during nasal delivery. The shield depicted in the paper is formed from flexible ethylene vinyl. The shield is custom trimmed and is custom fitted by heating to a malleable temperature and deformed by applied pressure.

Other possible mouthpiece designs are shown for example by use in self contained underwater breathing apparatus systems, for example as depicted in U.S. Pat. No. 4,862,909. This mouthpiece is a mouth guard type and is clamped between the teeth. A flange extends both in front of and behind the teeth.

Prior art mouthpieces are not well adapted for use in CPAP treatments because they are intended for conscious gripping by the user, and have been found subject to accidental removal with a user in a completely relaxed state such as sleep.

A further prior art mouthpiece that is of relevance is that shown in FIGS. 1 and 2, this mouthpiece is described in co-pending U.S. patent application Ser. No. 09/629,536. Referring to FIG. 1, the mouthpiece is illustrated including an extra-oral sealing flap 100 and intra-oral sealing flap 101. The extra-oral flap 100 in its natural bias is tapered from the breathing circuit connection 104; the wide-open end of which is shaped to conform to the facial contours around the outside of the mouth of a user. The extra-oral flap 100 is constructed of flexible material, such as silicone rubber. The outer flap 100 is seen in FIG. 2 in a bent back position. When the mouthpiece 102 is inserted into the mouth of a user, the outer flap 100 is intended to be in this bent back position to aid insertion. Prior to insertion, the outer flap is bent back by simply pressing on its outer periphery 106, until it snaps into the bent back position, in which it will stay unaided.

The mouthpiece as shown in FIGS. 1 and 2 also includes a tongue depressor 103 extending from the inner face of the intra-oral sealing flap 101. The tongue depressor 103 further includes a pair of vertically extending spacers 105 which in use may abut against the roof of the wearer's mouth and ensure that the tongue cannot completely block the air passageway. This stops the sleeping user unconsciously blocking the oral passageway and reverting to nasal breathing.

With the prior art mouthpiece of FIGS. 1 and 2, while the tongue depressor ensures that the tongue does not block the gases outlet, it prevents the user from moving their tongue to moisten the inside of their mouth, causing extreme dryness inside the user's mouth. Furthermore, the tongue depressor can prevent or restrict swallowing. Thus the mouthpiece of this invention has disadvantages that cause users discomfort.

SUMMARY OF THE INVENTION

It is an object of the present invention to provide a system for oral delivery of gases, and/or a mouthpiece for oral delivery of gases, which goes some way toward overcoming the above disadvantages or which will at least provide the public with a useful choice.

In a first aspect the present invention consists in a mouthpiece comprising:

a vestibular shield having an inner surface and an outer surface, said vestibular shield having a predetermined height which will overlap a user's teeth and gums when positioned in the mouth vestibule of a user;

gases passageway means extending from through said vestibular shield allowing for the passage of said gases through said mouthpiece;

extra-oral sealing means associated with said gases passageway to assist with compression upon a user's face, gases diffusing means associated with said gases passageway means and said inner surface that in use causes said gases to be diffused when exiting from said gases passageway.

In a second aspect the present invention consists in a system capable of being used for oral delivery of gases to a user comprising:
gases supply means,
a gases passageway in fluid communication with said gases supply means, and
a mouthpiece in fluid communication with said gases passageway including an intra-oral sealing means and an extra-oral sealing means and gases diffusing means.

In a third aspect the present invention consists in a system capable of being used for oral delivery of gases to a user comprising:
a mouthpiece,
a breathing tube,
decoupling means for connecting said mouthpiece to said breathing tube, and
means to diffuse gases associated with said decoupling means.

In a fourth aspect the present invention consists in a mouthpiece comprising:
a vestibular shield having an inner surface and an outer surface, said vestibular shield having a predetermined height which will overlap a user's teeth and gums when positioned in the mouth vestibule of a user,
gases passageway means extending through said vestibular allowing for the passage of said gases through said mouthpiece,
extra-oral sealing means associated with said gases passageway to assist with compression upon a user's face, and
adjustment means to alter the distance between said vestibular shield and said extra-oral sealing means.

In a fifth aspect the present invention consists in a mouthpiece comprising:
a vestibular shield having an inner surface and an outer surface, said vestibular shield having a predetermined height which will overlap a user's teeth and gums when positioned in the mouth vestibule of a user;
gases passageway means extending from through said vestibular allowing for the passage of said gases through said mouthpiece;
extra-oral sealing means associated with said gases passageway to assist with compression upon a user's face,
nose attachment connected to at least part of the upper edge of said extra-oral sealing means which in use covers or abuts said user's nose.

To those skilled in the art to which the present invention relates, many changes in construction and widely differing embodiments and applications of the invention will suggest themselves without departing from the scope of the invention as defined in the appended claims. The disclosures and descriptions herein are purely illustrative and are not intended to be in any sense limiting.

The invention consists in the foregoing and also envisages constructions of which the following gives examples.

BRIEF DESCRIPTION OF THE DRAWINGS

Preferred forms of the present invention will now be described with reference to the accompanying drawings.

DETAILED DESCRIPTION OF THE PREFERRED EMBODIMENTS

Figure 1:
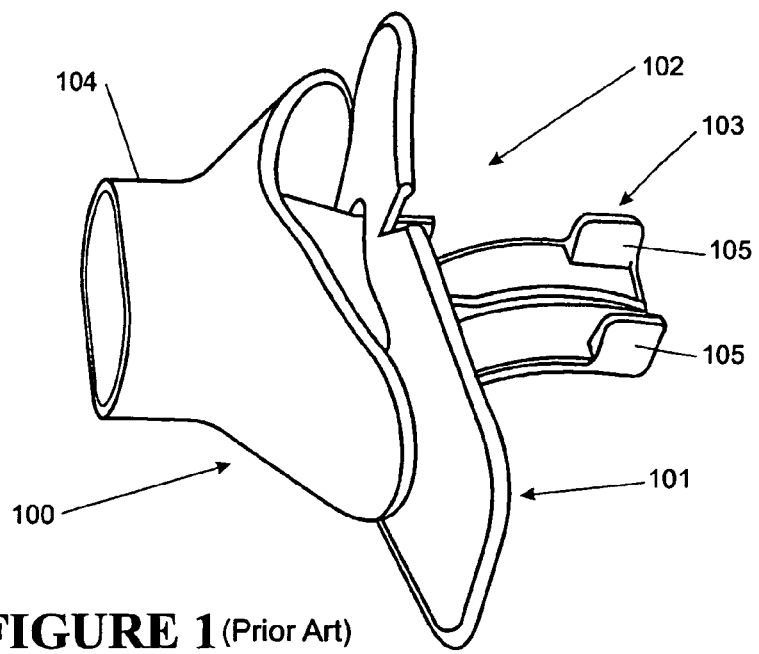
FIG. 1 is a perspective view of a prior art mouthpiece having an outer flap in an "in use" position.

While the invention may be susceptible to embodiment in different forms, specific embodiments are shown in the drawings and described in detail with the understanding that the present disclosure is to be considered an exemplification of the principles of the invention, and is not intended to limit the invention to that as illustrated and described.

Figure 3:
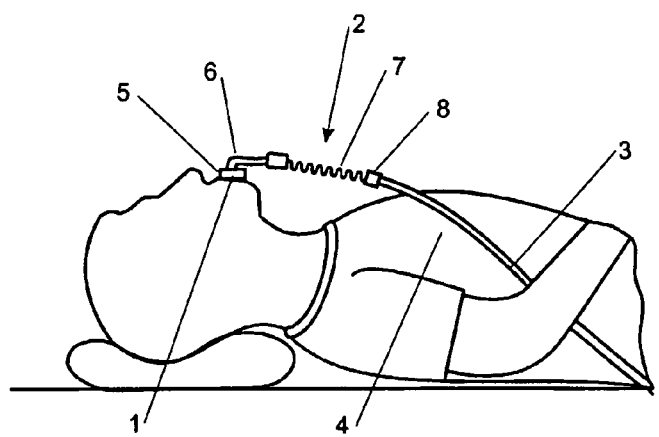
FIG. 3 is a side elevational view of the system according to the present invention as being used by a user.

The present invention provides a system for oral delivery of gases pressurised above ambient to a user and is especially suited for use in the oral delivery of air in continuous positive airway pressure (CPAP) treatments of sleeping disorders such as sleep apnoea. As shown in FIG. 3, the system includes a mouthpiece 1 which is connected by a connection 2 to a breathing circuit 3.

Gases Diffusing Shield

Figure 2:
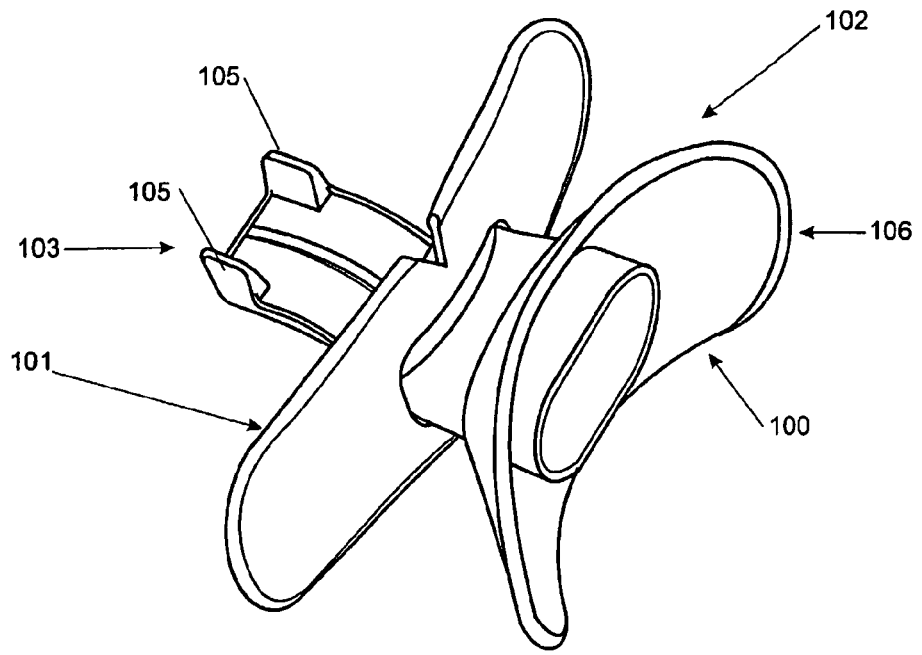
FIG. 2 is a perspective view of the prior art mouthpiece of FIG. 1 where the outer flap is bent back in a "locating" position.
Figure 4:
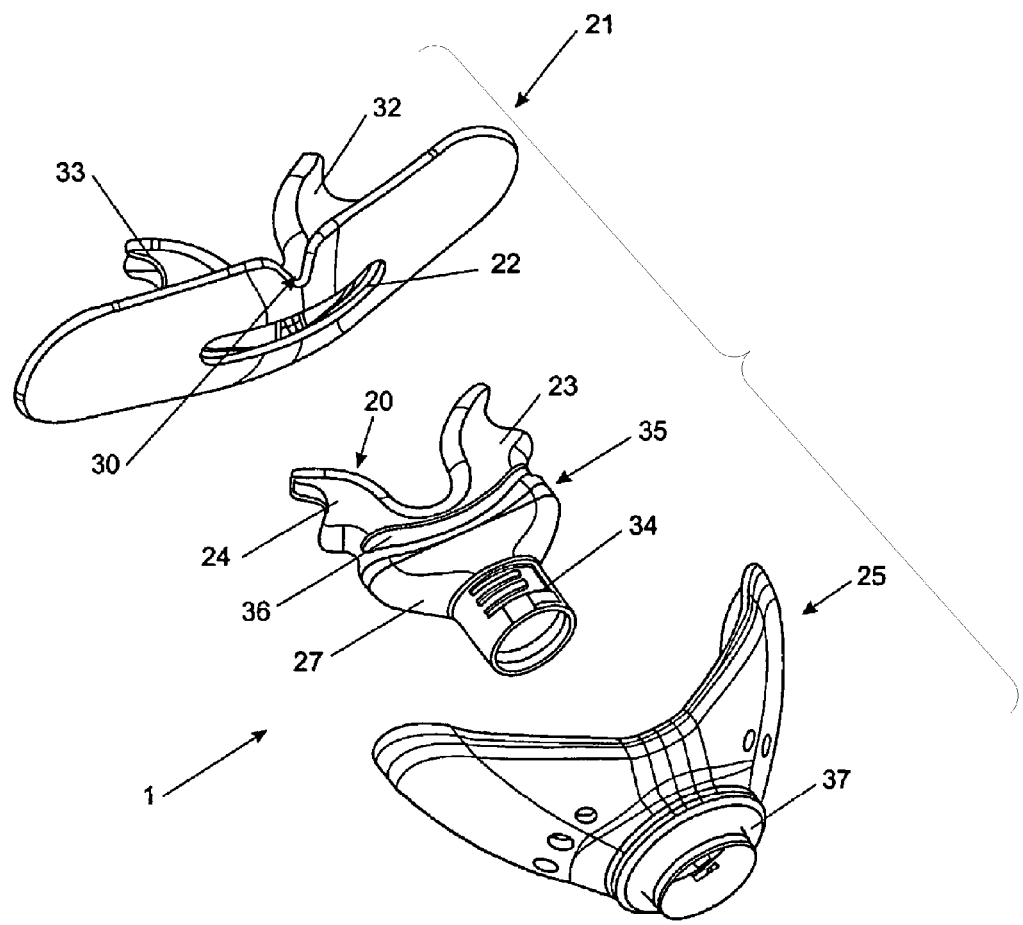
FIG. 4 is an exploded perspective view of a first form of the mouthpiece of the present invention including gases diffusing outlet.
Figure 5:
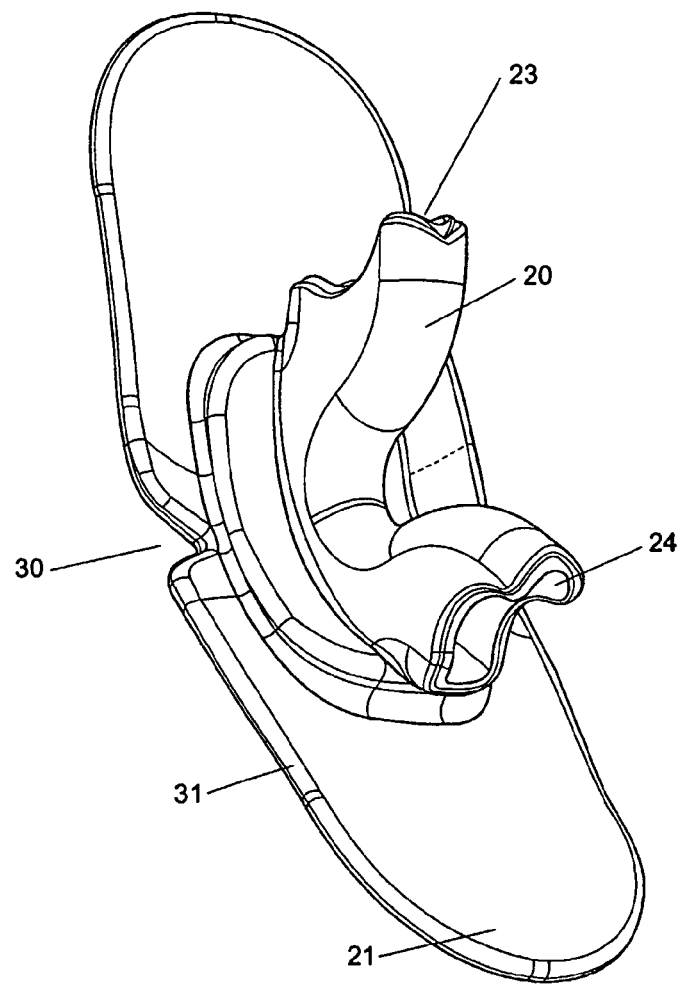
FIG. 5 is a perspective view of the vestibular shield of the first form of the gases diffusing mouthpiece of the present invention.
Figure 6:
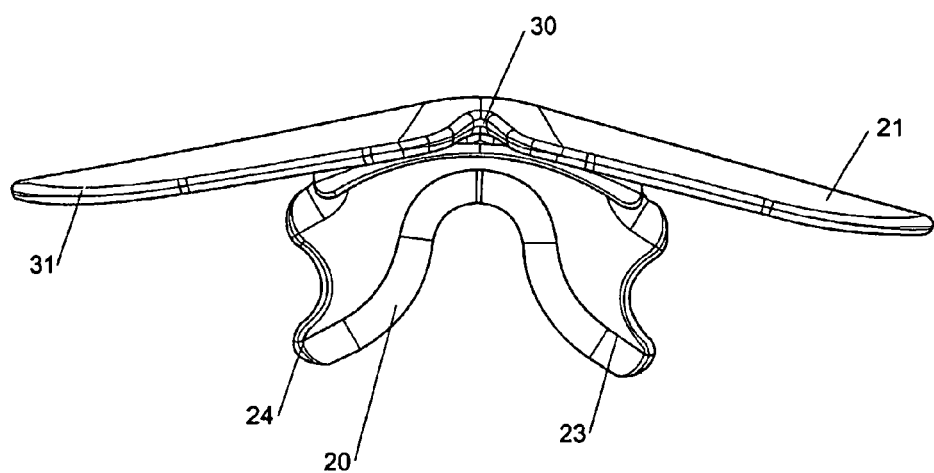
FIG. 6 is a plan view of vestibular shield of the first form of the gases diffusing mouthpiece of the present invention.

One preferred embodiment of the present invention is illustrated in FIGS. 4 to 6. In this embodiment, the mouthpiece 1 includes a vestibular shield 21 being a generally flat and generally rectangularly-shaped member in front elevation having a curved profile that reflects the curvature of a user's jaw and in turn the curvature of the labial vestibule region. A gases passageway extends through the vestibular shield from an inlet 22 to an outlet part 20 having two diffusing outlets 23, 24. The mouthpiece 1 also has an outer flap 25 similar to that described in relation to FIGS. 1 and 2 and that described in U.S. co-pending patent application Ser. No. 09/629,536.

The outer flap 25 is tapered and the wide open end is shaped to conform to the facial contours around the outside of the mask of a user. The narrow end terminates in an inlet 26 of substantially circular cross section and which is attached on one side to a breathing or inspiratory tube and the other to a connector 27 that connects the outer flap 25 to the vestibular shield 21. The connector 27 is made from a substantially rigid plastics material and broadens in cross-section from a circular end 34 to an elongated oval end 35 that is attached to the inlet 36 of the outlet part 20. In other forms of the present invention the connector may be formed in a soft plastics material such as silicon, so that it provides additional flexibility to the mouthpiece to enable the mouthpiece to better conform to the user's face.

The outer flap 25 and vestibular shield 21 are preferably formed in a soft and supple material such as silicon. The connector 27 between the outer flap 25 and vestibular shield 21, and outlet part 20 are made of a stiffer material, such as a hard plastics material, for example, polycarbonate. In the form shown in FIG. 4, attached to the outlet side of the vestibular shield 22 are over moulding outlets 32, 33 that are made from a supple material and that fit over the outlets 23, 24 of the outlet part 20. When assembled, as the vestibular shield 21 is made from a supple material, the outlet part 20 is able to be pushed through the inlet 22 in the vestibular shield 21 and the outlets 23, 24 fit into the over moulding outlets 32, 33.

The outlet part 20 is a substantially tubular U-shaped piece, where the top (or inlet 36) of the U is open and connected to the elongated end 35 of the connector 27. The arms of the U form gases passageways that are oval in cross-section that lead to the outlets 23, 24 that pass gases from the mouthpiece 1 into the user's mouth. In this manner the gases flowing through the mouthpiece 1 flow through the inlet to the outer flap 37, through the connector 27, and are diverted through each of the outlets 23, 24 and around the sides of the user's mouth. Hence the gases flowing into the user's mouth are effectively diffused.

The purpose of splitting or diffusing the gases flow in this manner is to prevent the user's tongue from covering the outlet and disrupting or stopping the gases flow and thus treatment provided to the user. If the prior art mouthpiece shown in FIGS. 1 and 2 had no tongue depressor to keep the user's tongue at the bottom of the user's mouth the user could inadvertently during sleep allow their tongue to cover the gases outlet. With a diff-used outlet such as that shown in FIG. 4 where at least two outlets direct flows substantially to the sides of the users mouth as opposed to the centre of the mouth it is not possible for a user to place their tongue inadvertently over both or even one of the outlets 23, 24. Furthermore with the absence of a tongue depressor and the diffusion of gases flow the user is still able to lift their tongue between the two arms of the outlet part and moisten their mouth, preventing dryness of the mouth. Also by allowing movement of the users tongue the mouthpiece of the present invention the user can swallow without difficulty. As a consequence of these advantages the mouthpiece in this form proves to be more comfortable to a user.

It is preferred that the outlet part 20 is made from a hard plastics material, but it could be made of a softer plastics material such as silicon.

It will be appreciated that as well as providing a substantially airtight seal the addition of the outer flap 25 provides enough compressive force on the mouth to keep the mouthpiece and conduit in place without the need for straps. This allows the administering of CPAP therapy to be considerably less obtrusive than traditional methods.

Figure 17:
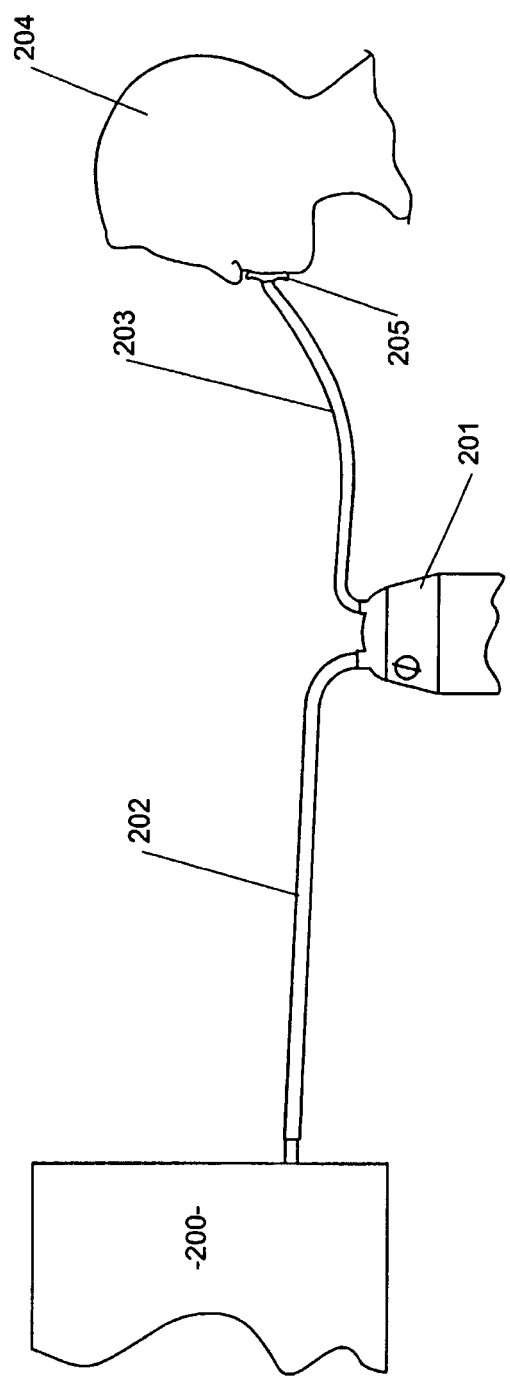
FIG. 17 is a block diagram of a respiratory system according to the preferred embodiment of the present invention.

A typical respiratory humidification circuit such as might employ the present invention is shown diagrammatically in FIG. 17, and includes the respirator 200, humidifier 201, and the associated respiratory breathing tubes 202 and 203. A user 204 under treatment is shown, with the mouthpiece of any of the abovementioned embodiments 205, located in the mouth of the user 204.

Figure 4A:
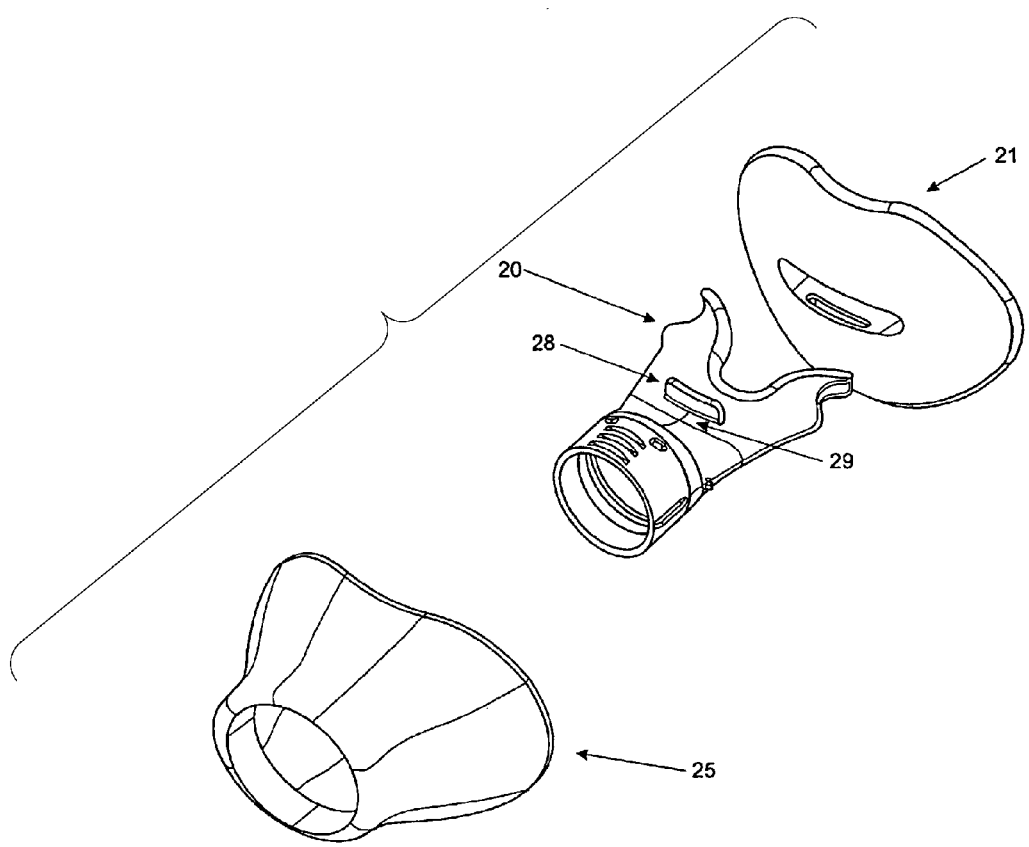
FIG. 4A is an exploded perspective view of a first form of the mouthpiece of the present invention, showing an abutment for use in locating and retaining the mouthpiece in the mouth of the user.

With reference to FIG. 4A, an abutment 28 and an area 29 are formed above the outlet part 20, preferably in the vestibular shield 21, is in which the user may place his or her teeth. The abutment 28 prevents inadvertent movement of the users' teeth away from or off the area 29. The abutment 28 also assists in the maintaining of the vestibular shield 21 between the users' lips and teeth retaining the mouthpiece in and about the users' mouth.

A notch 30 is provided centrally in the upper edge of the vestibular shield 21 to accommodate the upper frenal attachment. A slight bead 31 may be provided around the edge of the vestibular shield 21 for user comfort, with the vestibular shield 21 otherwise being very thin for additional suppleness.

Vestibular Shield with Apertures

Figure 7:
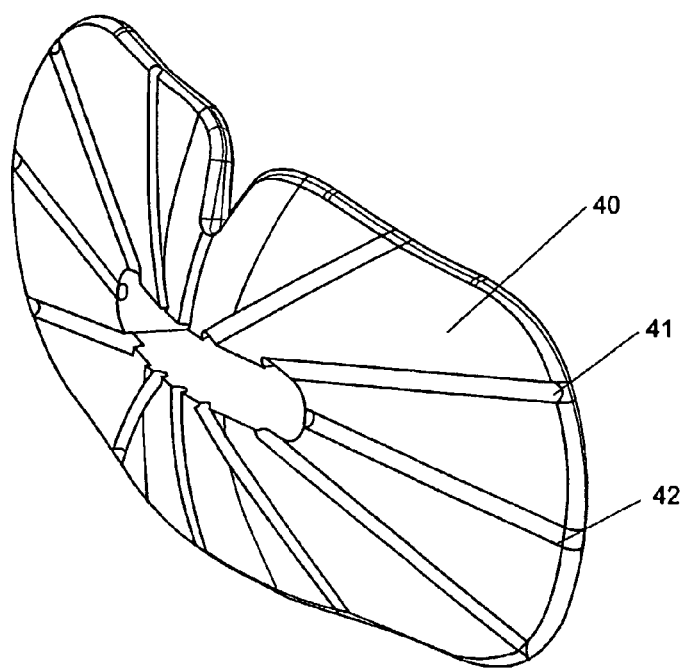
FIG. 7 is a perspective view of a vestibular shield having channels or apertures to allow for moisture flow about the shield.

In an alternative embodiment of the vestibular shield that may be used with the mouthpiece of the present invention is shown in FIG. 7. The vestibular shield 40 has a plurality of ventilation apertures 41, 42 extending out from the centre of the shield 40. The apertures are effectively channels spaced over the diameter of the shield 40 and are provided to allow moisture to move about the shield 40 to prevent dryness of the inside of the user's mouth.

As already discussed the vestibular shield 40 is preferably made of a soft and supple material, such as silicon. The shield 40 is preferably thin and has channels such as that shown in FIG. 7, although other forms of apertures or channels may be possible such as the shield being formed from a porous material or holes or slots being formed in the shield. It is preferred that the shield has a textured finish at least on its inside. The channels and the textured finish therefore allow for moisture to move around the vestibular shield and move from inside the shield to prevent dryness on the inside of the patient's mouth and to prevent the shield sticking to the inside of the patient's cheeks.

Figure 11:
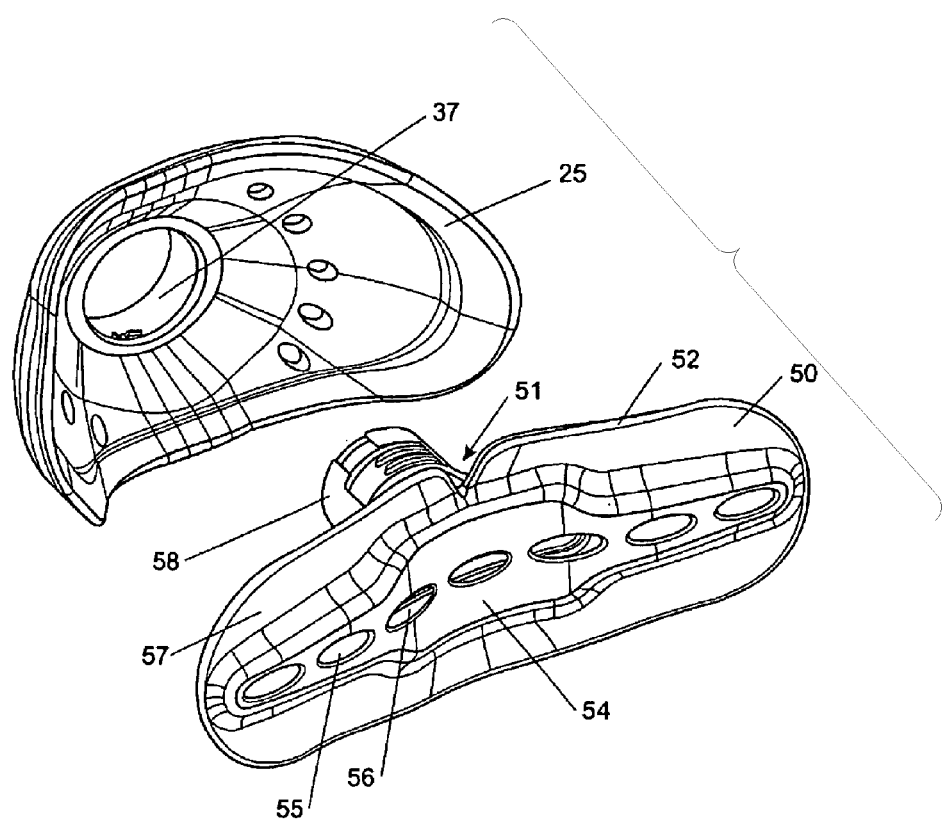
FIG. 11 is an exploded perspective view of a second form of the mouthpiece of the present invention having an alternative gases diffusing outlet.
Figure 12:
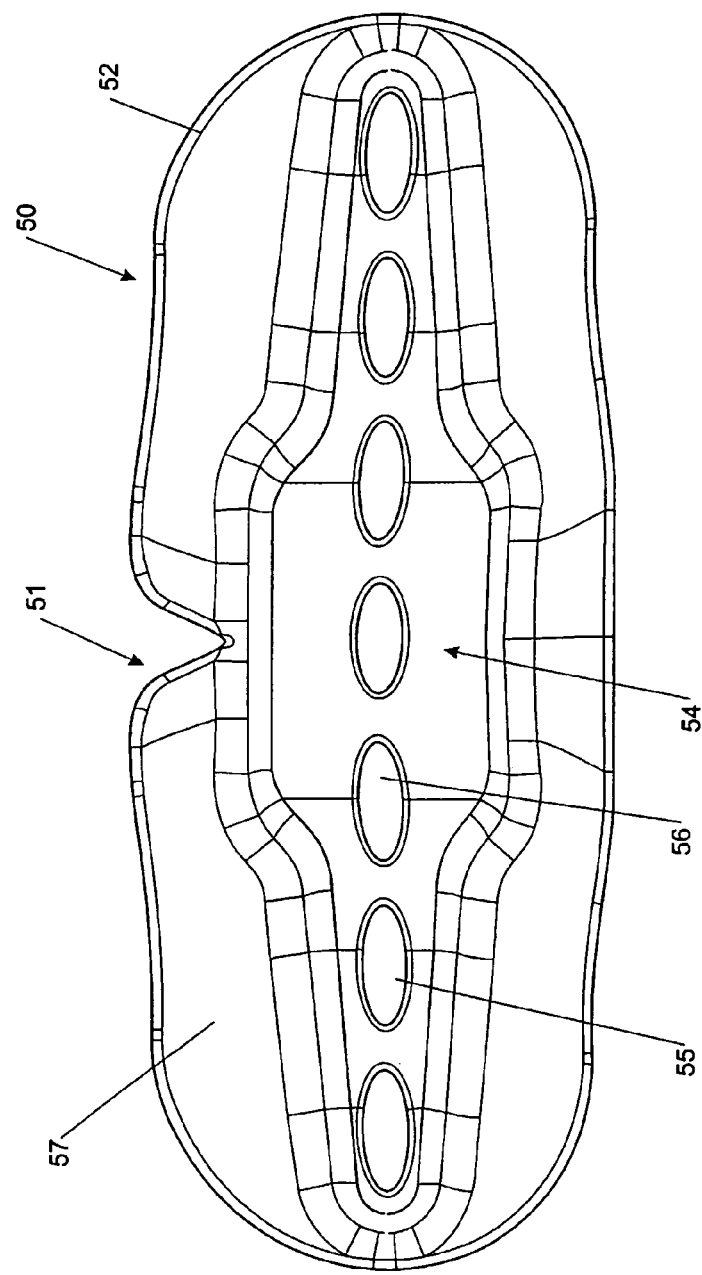
FIG. 12 is a side cross sectional view of vestibular shield of the first form of the gases diffusing mouthpiece of the present invention.
Figure 13:
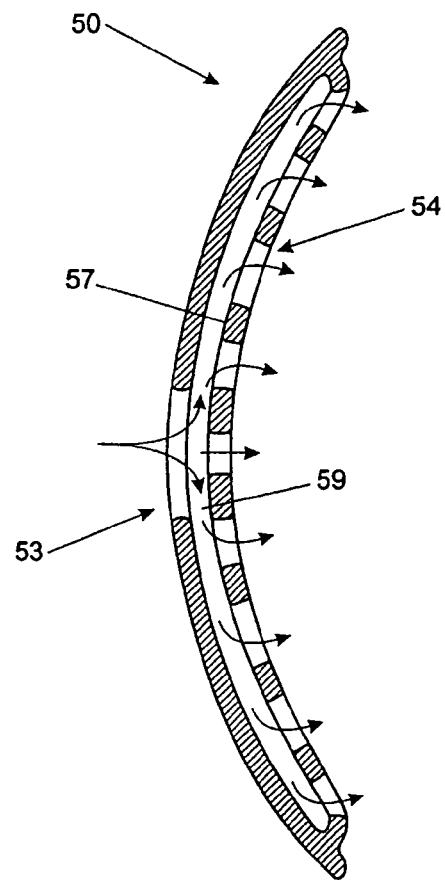
FIG. 13 is a side view of the vestibular shield of the second form of the gases diffusing mouthpiece of FIG. 11.

Another form of a vestibular shield having a diffusing outlet that may be used with the mouthpiece of the present invention is shown in FIGS. 11 to 13. This vestibular shield 50 is preferably used with the outer flap 25 as described above. The shield 50 has a notch 51 for the upper frenal attachment and may have a bead 52 provided around the edge of the shield 50, similar to that of FIGS. 4 and 7. A diffused outlet 54 is formed in the vestibular shield 50 such that gases received from the inlet 53 move into an elongated recess 58 formed in the central area of the shield 50. There are a number of outlets 55, 56 formed in the inner wall 57 of the shield 50. Extending from the outer wall of the shield 50 is a preferably tubular shield inlet 58 that is connected to the outer flap 25 via inlet 37, preferably by threaded connection, but other means of attachment may be used. In use, gases flow from the inlet 37 of the outer flap 25 through the shield inlet 58, into the elongated recess 59 formed in the central area of the shield 50 and out of the diffusing outlets 55, 56 into the user's mouth.

Adjustable Mouthpiece

Figure 18:
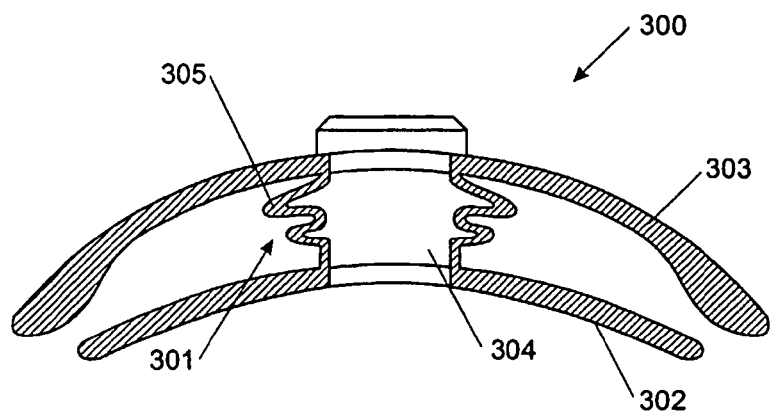
FIG. 18 is a cross-sectional plan view of a mouthpiece of the present invention including extendable means between the vestibular shield and extra-oral sealing means, where the extendable means is in a contracted position.
Figure 19:
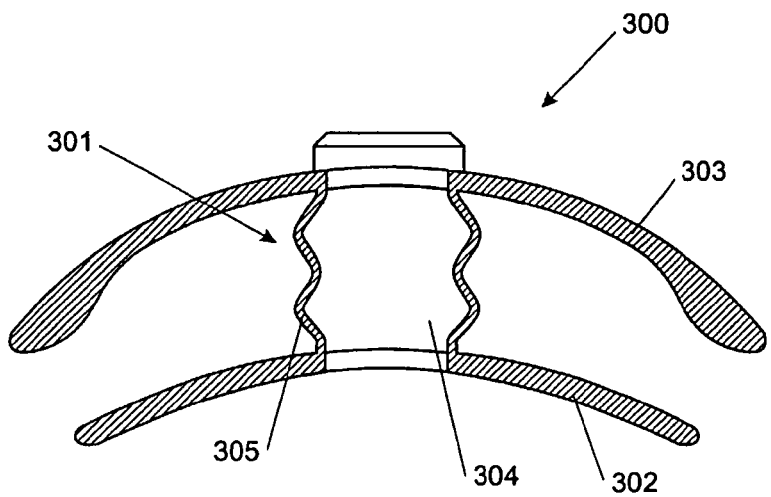
FIG. 19 is a cross-sectional plan view of a mouthpiece of the present invention including extendable means between the vestibular shield and extra-oral sealing means, where the extendable means is in an expanded position.

A further form of the mouthpiece of the present invention is shown in FIGS. 18 and 19. Here the mouthpiece 300 includes adjustment means 301 located between the vestibular shield 302 and outer flap 303 that allows for the distance to be altered between the shield 302 and flap 303, to allow for adjustment dependant on a user's facial contours. The adjustment means 301 is formed in the tubular gases passageway 301 between the vestibular shield 302 and outer flap 303. The adjustment means are bellows, corrugations or accordion like pleats 305 formed in the walls of said tubular passageway 304. The pleats 305 allow for the vestibular shield 302 and outer flap 303 to be moved apart or pushed together to accommodate varying user's mouths and facial contours. In use, the pleats 305 may be extended from a contracted position (as shown in FIG. 18) to a fully extended position (as shown in FIG. 19) and vice versa. Furthermore, the user may extend or contract the pleats 305 to any position in between the fully extended or contracted position and the mouthpiece 300 will stay in that position due to the stiffness of the material that the pleats are formed in. In the preferred form of this mouthpiece the tubular passage and pleats are formed in a stiff plastics material.

Figure 16:
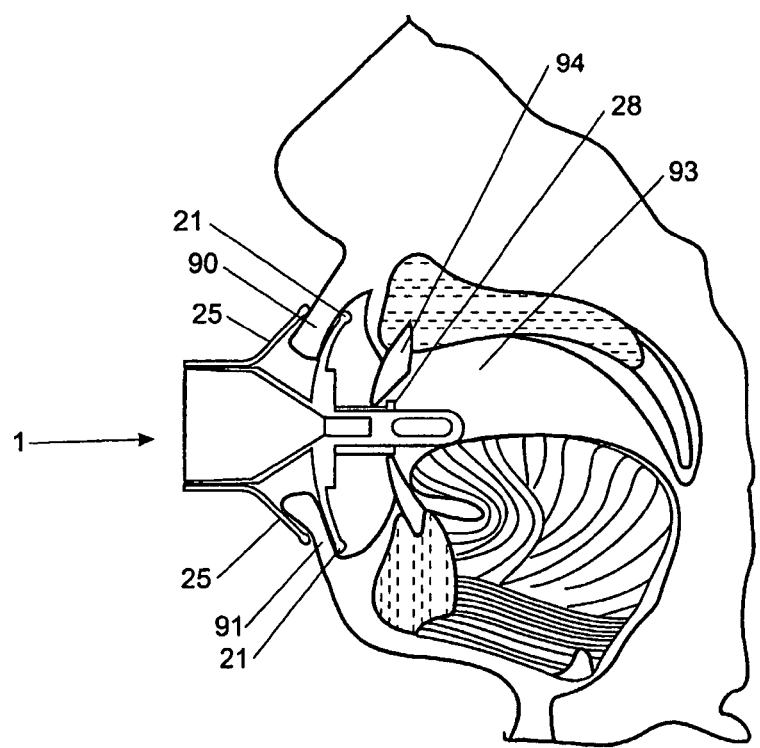
FIG. 16 is a cutaway view of the mouthpiece with split flow diffusing with an outer flap in use.

Referring now to FIG. 16, use of the mouthpiece according to FIGS. 4 to 6 is depicted. With the present mouthpiece 1, the vestibular shield 21 sits inside the user's lips 90, 91 and the outer flap 25 sits about the outside of the user's lips. Thus a seal is formed by the pressure caused by the outer flap on the outside of the users' lips and the opposing forces of the vestibular shield on the inside of the users' lips. Once the mouthpiece 1 is correctly positioned in the mouth 93, the outer flap 25 may be adjusted into its operational position by pressing on its outer periphery until it snaps back and depresses against the outside of the mouth. Due to the relative position of the vestibular shield 21 and the outer flap 25, the outer flap is unable to fully reach its natural bias and thereby inflicts the compressive force on the outside of the users' mouth.

As is illustrated in FIG. 16 the abutment 28 prevents the user's top row of teeth 94 from slipping from the mouthpiece and therefore assists in preventing accidental removal of the mouthpiece. Although not shown in FIG. 16, an additional abutment on the lower side of the mouthpiece may be provided to stop the lower row of teeth from slipping from the mouthpiece.

Figure 20:
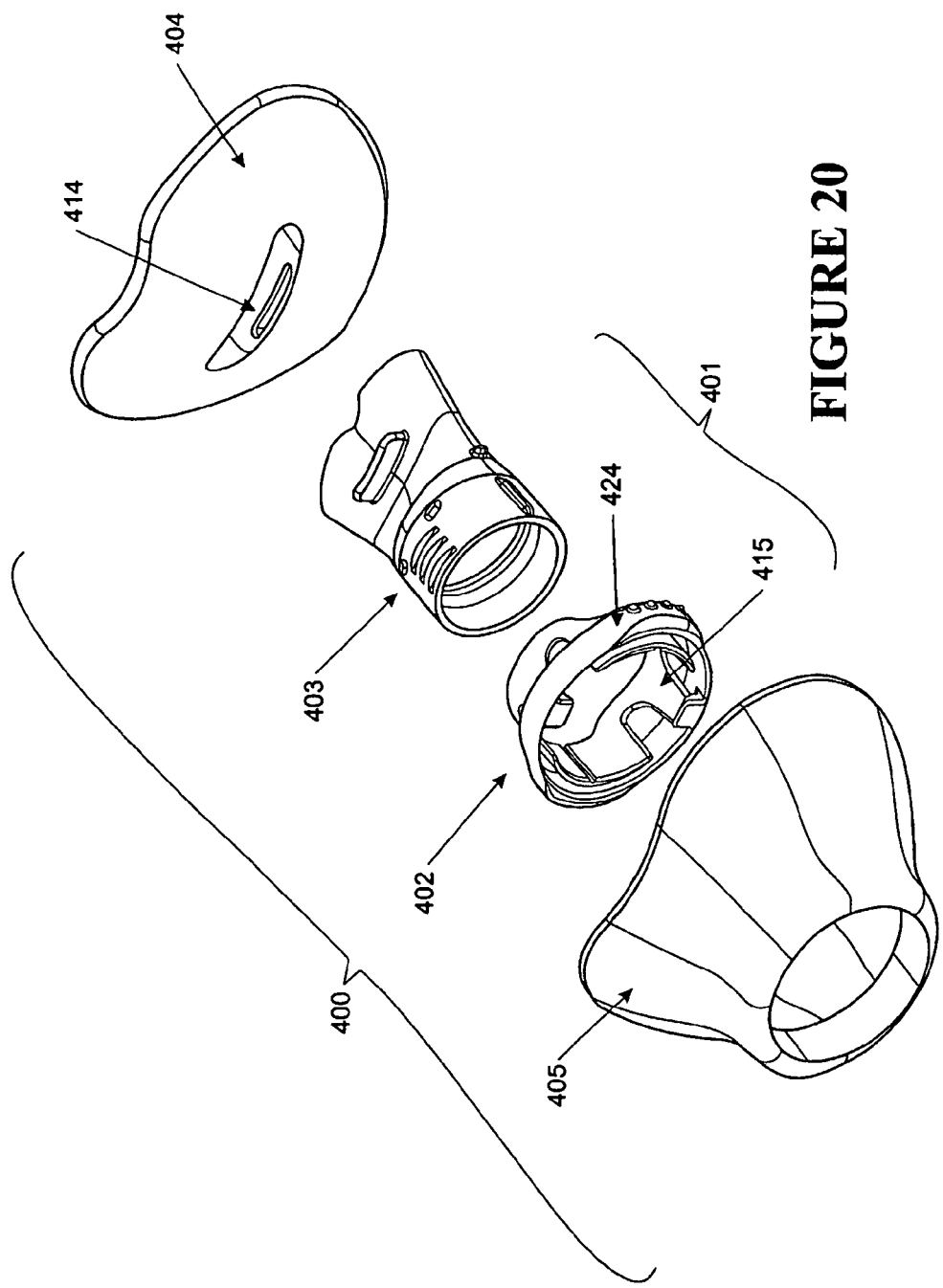
FIG. 20 is an exploded perspective view of an alternative form of the mouthpiece of the present invention including alternative extendable means between the vestibular shield and extra-oral sealing means.
Figure 21:
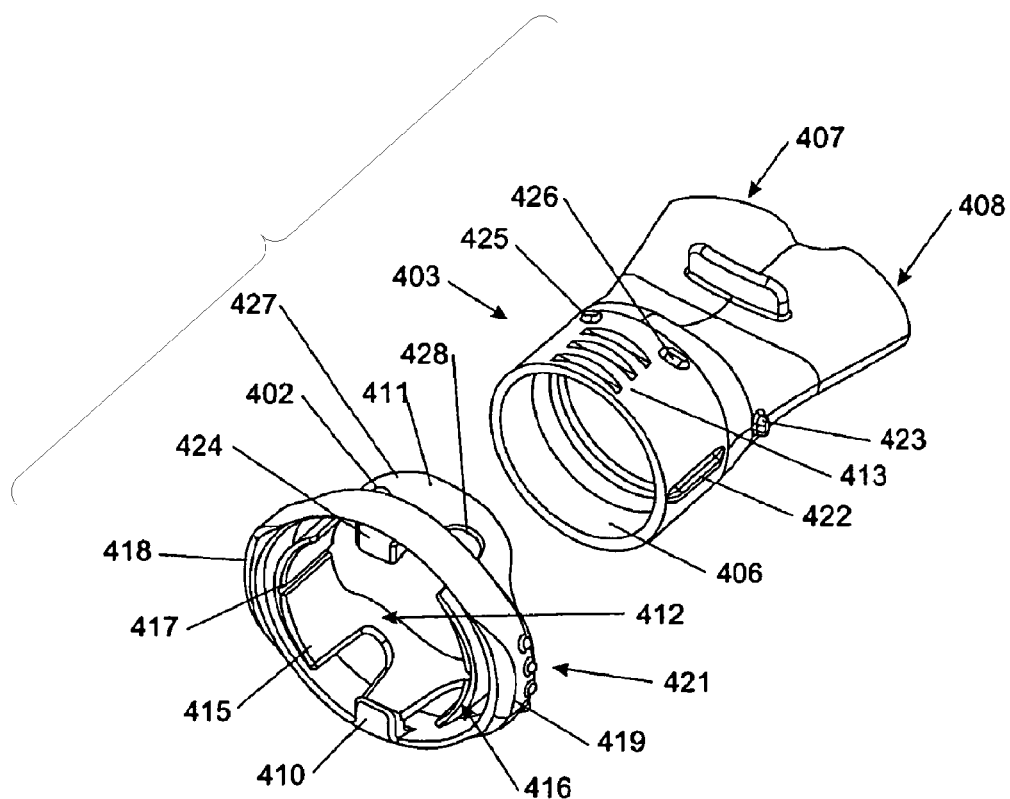
FIG. 21 an exploded perspective view of the alternative form of the mouthpiece of the present invention showing the gases passageway and sleeve that form the extendable means.
Figure 22:
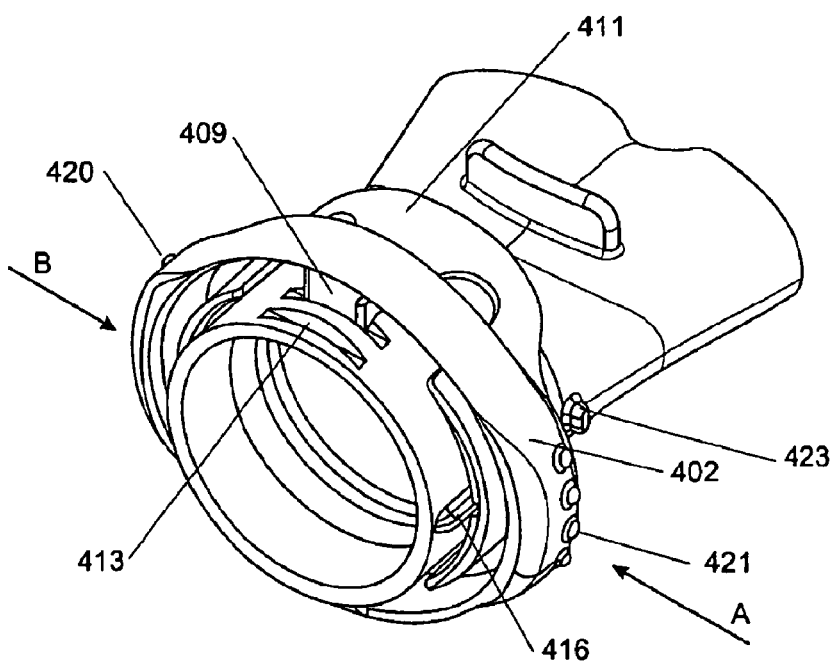
FIG. 22 is a perspective view of the alternative form of the mouthpiece of the present invention showing the gases passageway and sleeve in association.

An alternative form of the mouthpiece of the present invention is shown in FIGS. 20 to 22. Here the mouthpiece 400 includes an alternative adjustment means 401, to that shown in FIGS. 18 and 19. This form of the adjustment means 401 is the association of a sliding sleeve 402 with the tubular gases passageway 403. In this form the adjustment means 401 is located between the vestibular shield 404 and outer flap 405, and allows for the distance to be altered between the shield 404 and flap 405.

The sleeve 402 is attached to the flap 405 by way of an interference fit. Although not shown in the figures the flap 405 may during its moulding be over-moulded about the sleeve 402.

The gases passageway 403 shown in FIGS. 20 and 21 has at one end a circular opening 406 and the other end two oval exit ports 407, 408 that deflect gases passing through the mouthpiece to the sides of a patient's mouth, similar to those ports described in relation to FIGS. 4 to 6. The vestibular shield 404 is associated with the tubular passageway 403 by fitting the tubular gases passageway 403 through the aperture 414 in the shield 404. Due to the flexible nature of the material the shield 404 is made from, the shield 404 fits snugly about the tubular passageway 403, which does not allow for gases to leak through the aperture 414.

The gases passageway 403 has a series of elongate indentations 413 provided on its outer surface at its circular opening end 406. Although not shown, a set of diametrically opposed indentations similar to those indicated as 413 are provided on the passageway 403. The passageway 403 also has two diametrically opposed elongate protrusions (of which only one protrusion 422 is shown in FIGS. 20 and 21) located on its outer surface nearer the circular opening end 406. These elongate protrusions 422 are offset from the indentations 413 and are preferably spaced around the circumference of the gases passageway such that a 90 degree angle would be formed between each set of indentations and each elongate protrusion.

The gases passageway 403 also has at least one stop projection 423 located on its body. Preferably the stop projection 423 is integrally on the gases passageway 403 when it is moulded. The projection 423 abuts against the upper edge of the sleeve 402 and prevents the sleeve 402 from travelling too far along the gases passageway 403.

The sleeve 402 is preferably tubular in shape and made from a plastic material. The tubular shape of the sleeve 402 allows for the sleeve to be deformed, even though non-malleable plastics materials such as polycarbonate are used. To assist with the deformation of the sleeve 402 cantilever extensions 411, 412 are provided on the sleeve 402. These ensure that the sleeve can be deformed without the sleeve 402 cracking or breaking.

The sleeve 402 has an inner skirt 415 and an outer portion 424. The outer portion 415 is a circular tubular section that is integrally formed with the skirt 415. The skirt 415 has two protrusions 409, 410 that extend from the inner surface of the skirt 415 toward the central axis through the sleeve. In particular, during forming of the sleeve 402, the skirt 415 and outer portion 424 are fused together at the protrusions 409, 410. The protrusions 409, 410 are formed on one outer edge of the skirt 415 and link to the outer portion 424. The cantilever extensions 411, 412 are integrally formed on the other edge of the skirt 415 during moulding and key hole apertures 427, 428 are formed in the skirt 415 that extend partially into the cantilever extensions 411, 412. The purpose of the key hole apertures 427, 428 are to prevent the sleeve 402 from disengaging from the gases passageway 403 after being assembled. Once the sleeve 402 is assembled about the gases passageway 403 the nodules 425, 426 are located within the key hole apertures 427, 428 and are able to slide within the apertures 427, 428, but prevent the sleeve 402 being removed from the gases passageway 403 as they abut against the ends of the apertures 427, 428. Although not apparent in FIGS. 20 to 22, complimentary keyhole apertures and nodules are provided on the diametrically opposed sides of the gases passageway 403 and sleeve 402.

Each of the protrusions 409, 410 and extensions 411, 412 are formed on diametrically opposed sides of the sleeve 402. Elongated apertures 416, 417 are formed on the inner surface of the skirt 415. The apertures 416, 417 are diametrically opposed and are formed in the skirt 415 at a position on the circular skirt that is 90 degrees from the diametrically opposed protrusions 409, 410.

The outer portion 415 of the sleeve 402 has regions 418, 419 that are diametrically opposed and are thicker in width than the rest of the outer portion. These regions 418, 419 are effectively finger pads that may be provided with small protrusions 420, 421 or the like that allow for traction between a user's fingers and the regions 418, 419.

The regions 418, 419 are offset from the protrusions 409, 410 such that if sidewise forces A and B (shown in FIG. 22) are placed on the finger pad regions 418, 419 the sleeve is deformed from a circular shape to a more elongated oval shape. As the regions 418, 419 and protrusions 409, 410 are offset from one another when the regions are depressed or squeezed together the protrusions 409, 410 on the sleeve 402 are pushed upwards and away from each other.

When assembled, the mouthpiece of the alternative form as shown in FIGS. 20 to 22, the sleeve 402 fits about the tubular passageway 403. The sleeve is prevented from moving to the exit port end of the passageway 403 by the edge of the sleeve 402 abutting the projections 423. The fitting of the elongate protrusions 422 into the elongated apertures 416, 417 formed in the inner skirt 415 of the sleeve 402 prevent rotation of the sleeve 402 and outer flap 405 relative to the gases passageway 402.

In use, a user may adjust the mouthpiece 400 by squeezing the regions 418, 419 wherein the protrusions 409, 410 extending from the inner surface of the skirt 415 are released from one of the indentations 413. The user may then slide the sleeve 402 and outer flap 405 along the gases passageway 402 and release the regions 418, 419 whereby the protrusions 409, 410 will be released back into an alternative one of the indentations 413. Therefore, the distance between the shield 404 and outer flap 405 can be reduced or increased depending on the user's requirements in this manner. In the preferred form there are three indentations 413, as shown in FIG. 20, where each of these relates to one of three positions that a patient can adjust the distance between the shield 404 and outer flap 405. In other forms of the mouthpiece 400 the gases passageway may be provided with any number of indentations.

Figure 25:
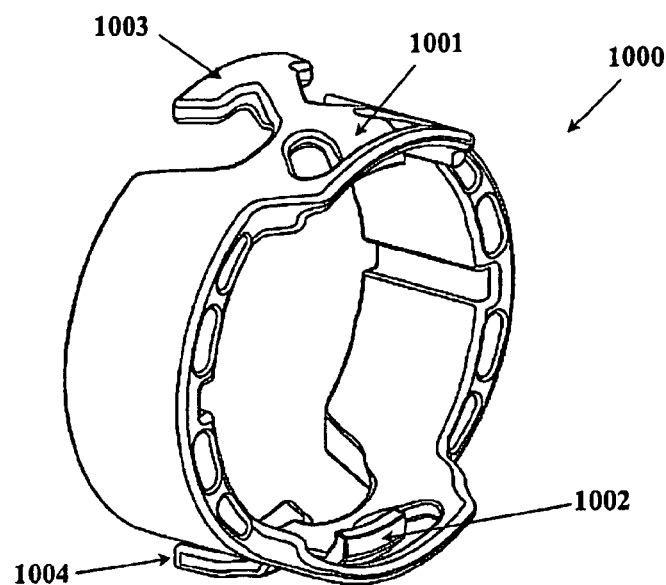
FIG. 25 is a perspective view of another alternative embodiment of a mouthpiece with an alternative adjusting mechanism between the outer flap and vestibular shield.

Referring now to FIG. 25, a further form of the adjustment mechanism is shown. The adjustment mechanism may be similar to that described above, but having a different locking mechanism. For example, the mouthpiece would be very similar to the form of that shown in FIG. 21, but the slideable sleeve 402 of FIG. 21 would be replaced by the alternative sliding sleeve 1000. Thus the slideable sleeve 1000 would be fitted to a similar tubular passageway 403 as shown in FIG. 21. The sleeve 1000 has a similar working mechanism to that of the slideable sleeve 402 and has protrusions 1001, 1002 that fit into the apertures 413 on the tubular passageway 403, which cause locking of the slideable sleeve 1000 on the passageway 403 (compare with protrusions 409 on FIG. 21). The protrusions 1001, 1002 can be caused to move out of the apertures 413 by placing an inward force on complimentary and opposing flexible protrusions 1003, 1004. Therefore, when a user squeezes the flexible protrusions 1003, 1004, the locking protrusions 1001, 1002 move out of one of the apertures 413. The sleeve 1000 can then be slid along the tubular passageway 403 and the flexible protrusions 1003, 1004 released, causing the locking protrusions 1001, 1002 to enter another of the apertures 413. This causes the distance between the outer flap and vestibular shield to be adjusted.

Figure 26:
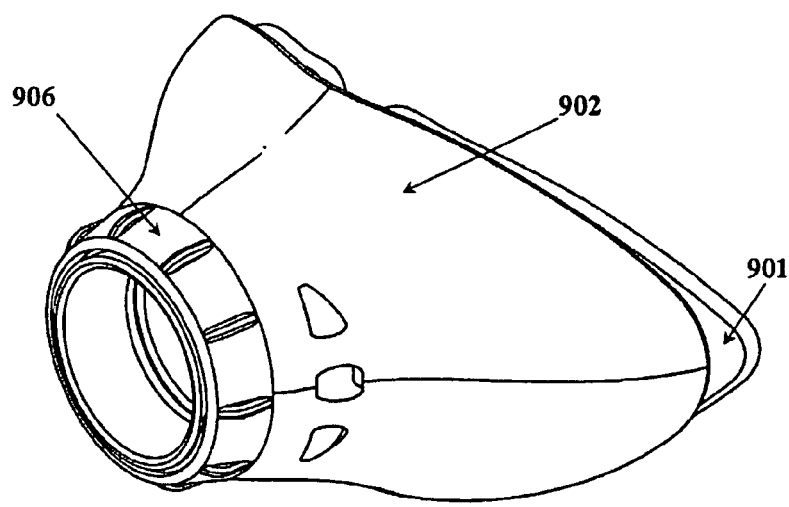
FIG. 26 is a perspective view of a further alternative embodiment of the mouthpiece of the present invention where the mouthpiece has yet another form of threaded adjustable mechanism to adjust the distance between the vestibular shield and outer flap.
Figure 27:
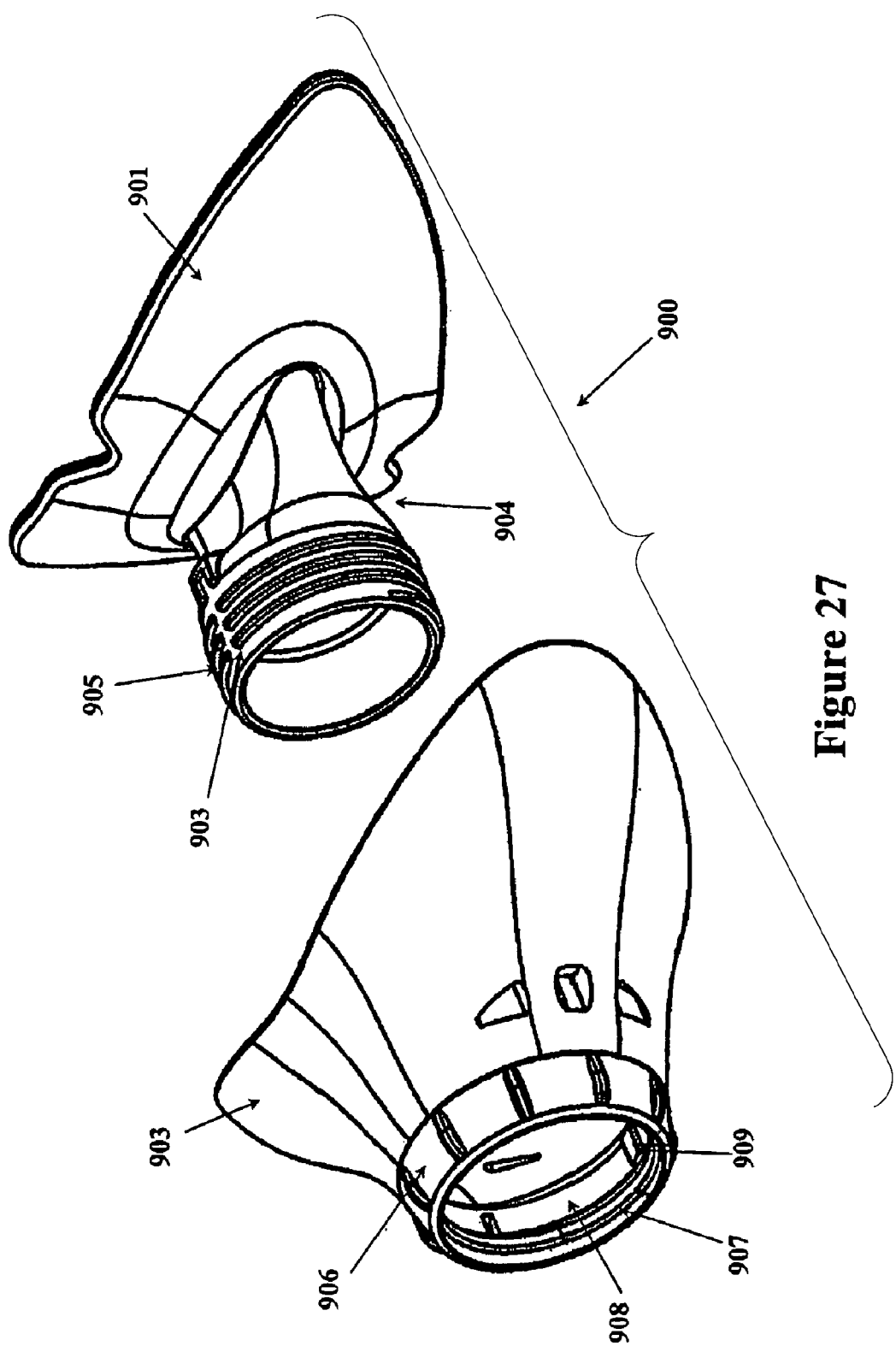
FIG. 27 is a perspective partially exploded view of the mouthpiece of FIG. 26.
Figure 28:
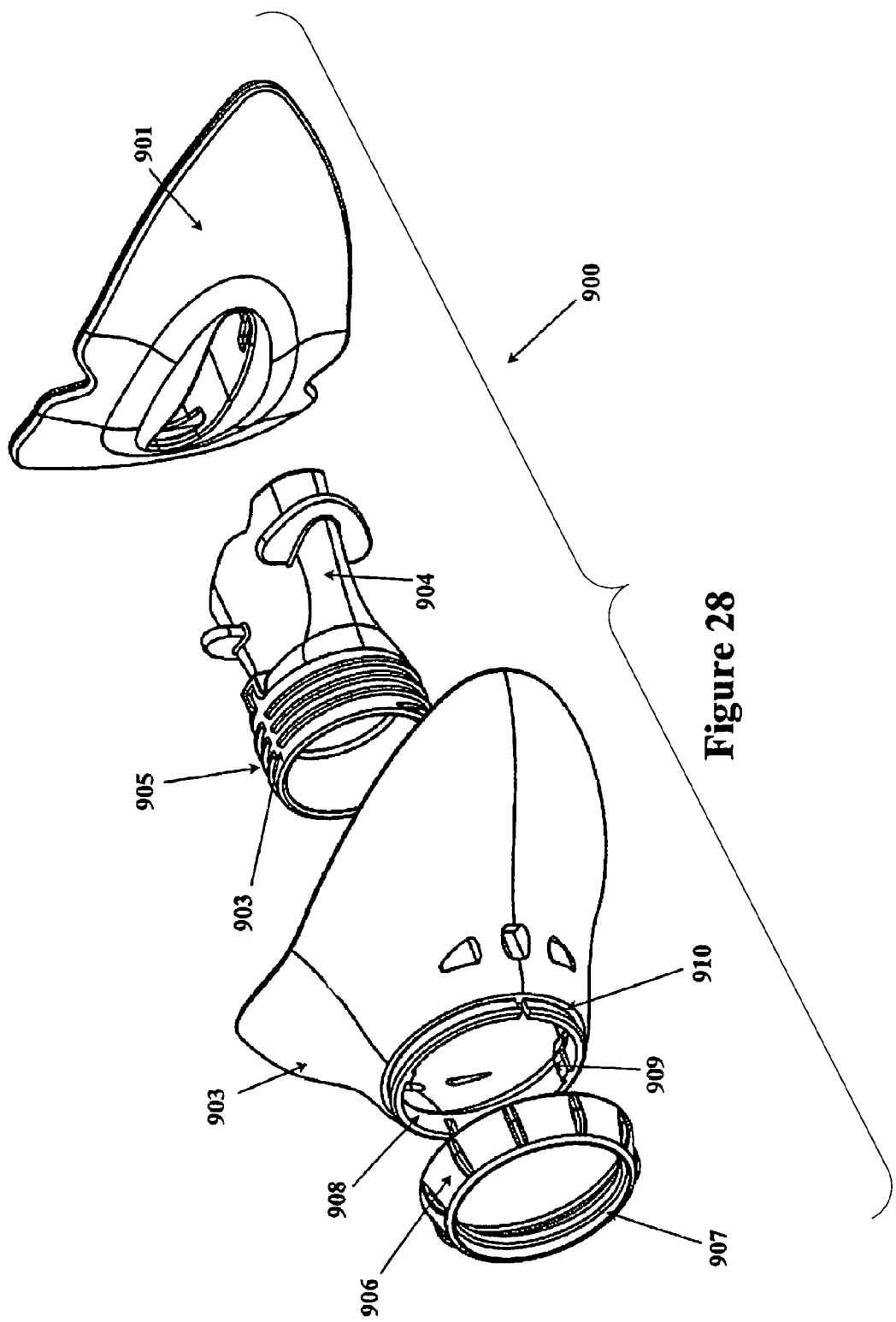
FIG. 28 is a perspective fully exploded view of the mouthpiece of FIG. 26, showing an over moulded ring attachment on the outer flap.

Yet another form of adjustment mechanism between the vestibular shield and outer flap is shown in FIGS. 26 to 28. Here the mouthpiece 900 has an adjustment mechanism or means that is a threaded connection, which allows for the distance to be altered between the vestibular shield 901 and outer flap 902, to allow for adjustment dependent on a user's facial contours. A thread is formed in the tubular gases passageway 904 between the vestibular shield 901 and outer flap 902. The outer flap 902 has a moulded ring or bezel 906 having an inner thread 907. The ring 906 is preferably permanently attached (for example, clipped to) a ring attachment means 908 in which the outer flap 902 is over moulded about. The ring or bezel 906 is capable of rotating about the ring attachment means 908. As described the outer flap 902 is moulded over the ring attachment means 908. The edge 910 of the moulded outer flap 902 may extend out from the ring attachment means 908 to create interference between the outer flap 902 and the ring 906. Therefore, the amount of friction created between the ring 906 and the outer flap 902 can be controlled dependent on how far out the outer flap 902 extends. The friction created prevents the ring 906 from freely rotating.

In use, the ring attachment means 908 is slid about the threaded gases passageway 904 and causes the outer flap 902 and shield 901 to be aligned by the alignment of a protrusion 909 on the tubular passageway 904. The protrusion 909 is aligned with and runs along the track 903 formed in the thread 905 on the tubular passageway 904. As the tubular passageway 904 and ring attachment means 908 are both made from a hard plastics material (such as, polycarbonate) they can be slid against one another. The thread 907 on the ring 906 meets with the thread 905 on the passageway 904 and by rotating the ring 906 on the ring attachment means 908, the ring attachment means 908 and outer flap 902 are moved towards the vestibular shield 901. As the threaded ring 907 progresses along the threaded passageway 904 the distance between the vestibular shield 901 and outer flap 902 is reduced or increased dependent on the user's requirements. The capability of the ring 906 to rotate on the ring attachment means 908 means the distance between the vestibular shield 901 and outer flap 902 can be altered into an infinite number of positions.

The mouthpiece embodiments described above that provide for fitting or adjustment of the distance between the outer flap and vestibular shield all allow for adjustment while a patient's is wearing the mouthpiece. Therefore, one inserted in the patient's mouth the adjustment mechanism can be used to tighten or loosen the mouthpiece to allow for optimum patient comfort while maintaining the compressibility between the shield and flap to retain the mouthpiece in the patient's mouth.

Elbow Connector

Attention is now directed to FIG. 3. It has been found that an additional factor in the effectiveness of any mouthpiece, including mouthpiece 1, is the manner in which the mouthpiece is connected to the breathing circuit 3. The weight of the breathing circuit 3, and any attempted movement of one other of the breathing circuit 3 and the mouthpiece 1 relative to the other, is one of the largest influences tending to dislodge a mouthpiece 1 from the mouth of a user. It must be noted that the mouthpiece 1 must remain in position and maintain a seal during all sleep when the user has no muscle tone.

The connection 2 as provided in the present invention between the breathing circuit 3 and the mouthpiece 1 decouples the mouthpiece 1 from the breathing circuit 3. As a result, the connection 2 is effective in reducing the forces placed on the mouthpiece 1 by the breathing circuit 3 when the user moves around during sleep. In the preferred sleeping position, the breathing circuit 3 is laid across the chest 4 of the user, and may be secured to the user's bed clothes or sleeping garments. The breathing circuit 3 is preferably laid on the chest of the user to take the weight of the breathing circuit 3 off of the mouthpiece 1.

To connect between the gases outlet 5 which is vertical when the user is lying on his or her back and the breathing circuit 3 which is generally horizontal, an L-shaped elbow 6 is incorporated in the connection 2. The elbow 6 is formed at a right angle and provides a positive pressure on the mouthpiece 1 to maintain the mouthpiece 1 in the user's mouth. The elbow 6 may include a swivel joint and may be disconnected from gases outlet 5. The connection 2 further includes an extremely flexible connecting tube 7 provided between the elbow 6 and the breathing circuit 3. The connecting tube 7 is preferably connected to the breathing circuit 3 by a swivel joint 8. The elbow swivel joint 6 allows for movement of the connection tube 7 relative to the mouthpiece 1. The swivel joint 8 allows for movement of the connection tube 7 relative to the breathing circuit 3. It is to be understood that one or both of the swivel joints 6, 8 could be eliminated, but the preferred embodiment includes swivel joint 8.

Figure 14:
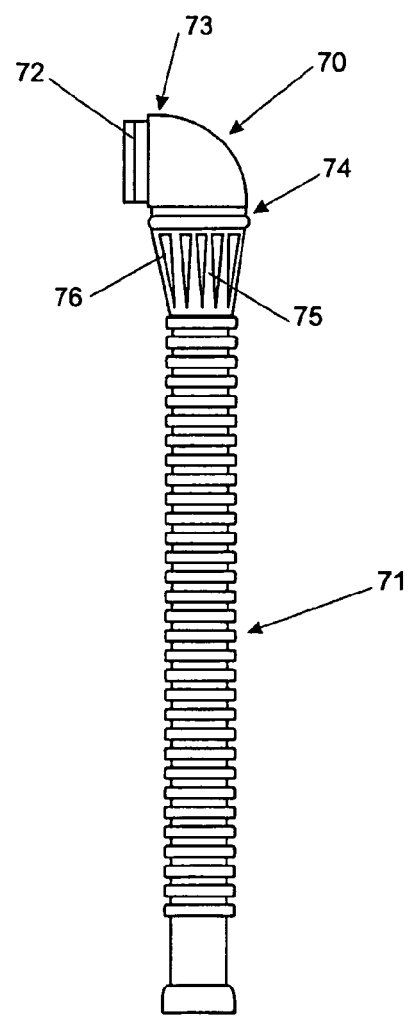
FIG. 14 is a side view of an elbow piece and associated tubing, connectable and to be used with any one of the embodiments of the mouthpiece of the present invention.

Referring to FIG. 14 an alternative form of the elbow described above is shown. In this form the elbow piece 70 is shown as attached to a connecting tube 71. The elbow piece 70 has an outlet 72 attached to the inlet of a mouthpiece (37 on FIG. 4) such that gases flow through the connection tube 71 through the elbow piece 70 and out the outlet into the mouthpiece and subsequently into the user's mouth. The elbow piece is substantially L-shaped and preferably includes a swivel joint 73. Additionally a swivel joint may be provided on the connecting tube side of the other connector, namely swivel joints 74. The end 75 distal to the outlet is substantially tubular in shape and tapers from a wider diameter at the joint 74 and narrows towards the connecting tube 71 disposed along the length of a diff-using part 75 are elongate apertures 76 that are also preferably tapered and shaped rather at the joint 74 end and narrowing toward the connecting tube 71. A plurality of these apertures 76 are disposed about the diffusing part and allow for gases exhaled by the user through the mouthpiece and outer connector to diffuse into the ambient air. The tapered apertures also have the additional advantage of diffusing the gases in a direction along the connection tube 71 and therefore away from the user. Also these gases flow away from anyone who may be facing the user, such as the user's partner, for example, during sleeping. Additionally the diffuser 75 also allows for low noise diffusion of exhaled gases.

Figure 15:
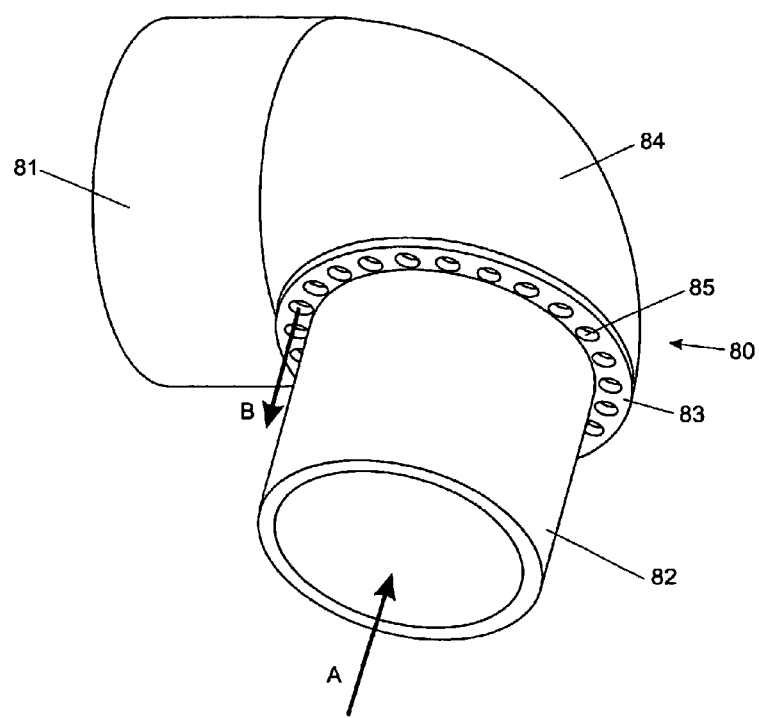
FIG. 15 is a perspective view of a further form of an elbow piece, connectable and to be used with any one of the embodiments of the mouthpiece of the present invention.

Referring now to FIG. 15, which shows a further alternative form of an elbow that may be used with a mouthpiece of the present invention. The elbow 80 again is substantially L-shaped and connects at an outlet end 81 to the inlet of a mouthpiece. The inlet 82 is connected to a connecting piece of tube such as that shown in FIG. 3 or the connecting tube 71 of FIG. 14). In this embodiment the elbow connector 80 has diffusing means formed on a ledge 83 formed by the reduction in the diameter from the body 84 of the elbow 80 and the inlet piece 82. In use gases flow in through the inlet 82 in the direction of arrow A and exhaled gases are diffused out the plurality of apertures formed about the circular ledge 83 (although only one aperture 85 is labelled it is preferred that a number of apertures are formed about the circular ledge. Due to the high pressure of the incoming gases the lower pressure outgoing gases cause less effect as they are pushed to the edges and out the apertures 85 on the incoming disk in the direction of arrow B. Again, like the embodiment of the other as shown in FIG. 4 the exhaled gases are directed away from the user and the user's partner and the noise of gases diffusing is reduced.

Nose Flap and Attachments

Figure 8:
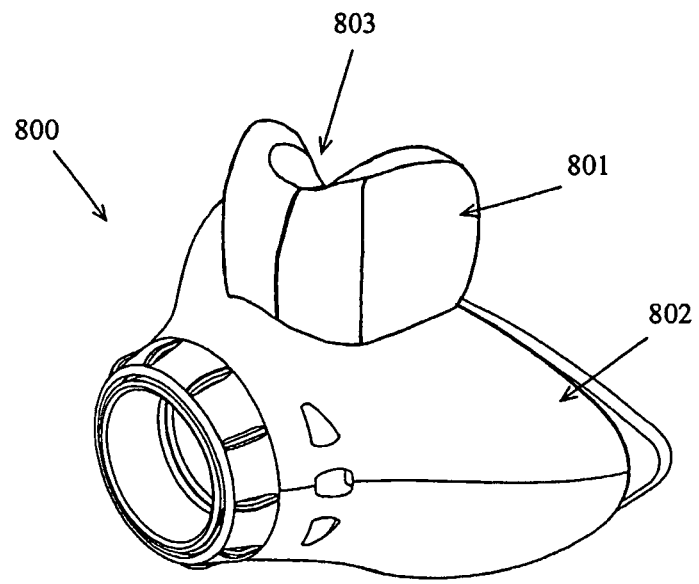
FIG. 8 is a perspective view of a mouthpiece having
Figure 9:
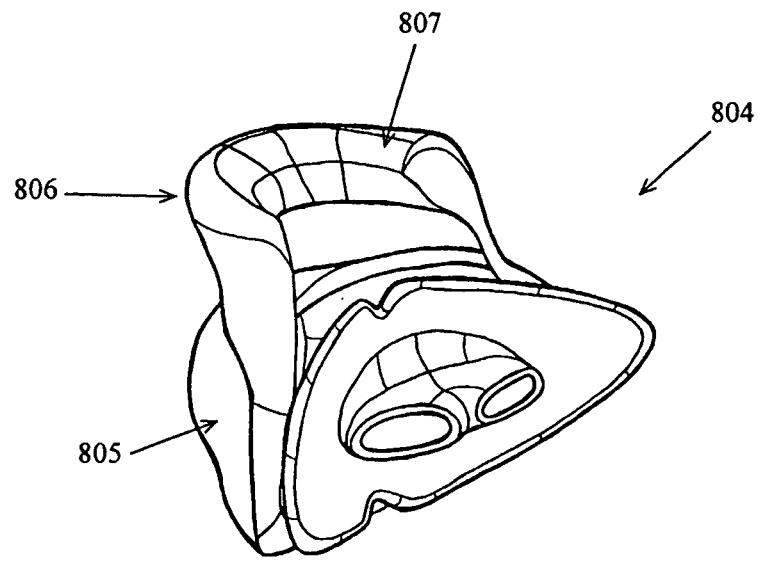
FIG. 9 is a perspective view of a mouthpiece with an outer flap having an integral nose flap.
Figure 10:
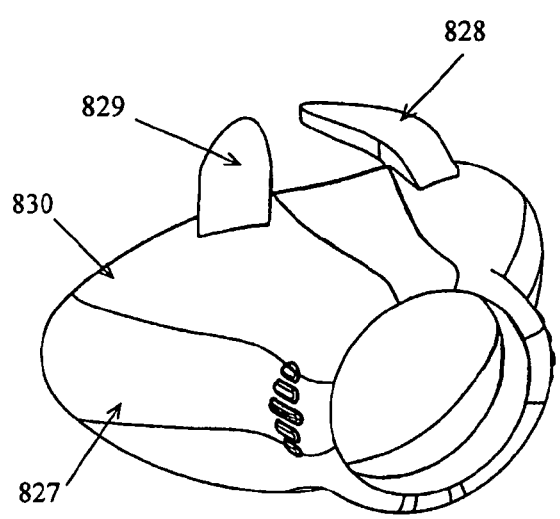
FIG. 10 is a perspective view of an alternative embodiment of an outer flap that has protrusions that assist in closing off a patient's nasal passages.

Reference is now made to FIGS. 8 to 10 in which further embodiments of a mouthpiece with nose flap or other attachments are illustrated.

Referring first to FIG. 8 a mouthpiece 800 is shown that has a blocking member or attachment 801 extending from the outer flap 802. The blocking member 801 has a curved or cut out region 803 such that when the mouthpiece is in use in a patient's mouth the blocking member 801 rests against the patient's nose and blocks off the patient's nostrils. The blocking member 801 has the purpose of preventing leakage of gases from the patient's nose when they are receiving treatment, such as receiving continuous positive pressure gases, via the mouthpiece. In the preferred form of this mouthpiece 800 the blocking member 801 is integrally formed with the outer flap in silicone. In other forms the blocking member may be made from other materials, such as foam, and separately attached, by way of gluing or the like, to the outer flap.

Figure 9A:
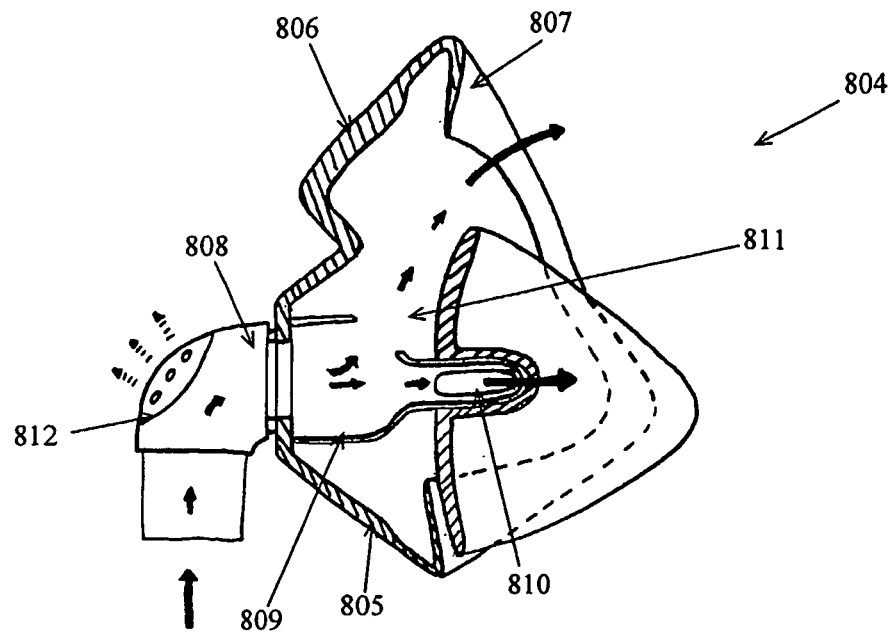
FIG. 9A is a cross sectional view of the mouthpiece of FIG. 9.

In another embodiment, as shown in FIGS. 9 and 9A, a mouthpiece 804 may be provided with an outer flap 805 having a nose flap 806 that in use extends over and about the patient's nose. The nose flap 806 is moulded with the outer flap 805, preferably out of silicone, but other appropriate materials may be used. The nose flap 806 is contoured to the approximate shape of the human nose and has a lip or flange 807 around its edge to assist in the sealing of the nose flap 806 about a patient's nose, so as assist in the preventing of leaks from the nose. The lip or flange 807 continues around the perimeter of the outer flap to assist in sealing of the flaps against the user's face.

In FIG. 9A we see a cross-section of the mouthpiece 804 of FIG. 9 with gases flowing through it shown by arrows. The gases flow from the tubing (such as the conduit 3, shown in FIG. 3) through an elbow connector 808 and into the tubular passageway 809. The tubular passageway 809 has two outlets in it, one outlet 810 that causes gases passing through the passageway 809 to be directed to the oral cavity and other outlet 811 to the nasal cavities. In this manner the patient has the option of breathing gases through either their nose or mouth. Expired gases from the patient are expelled through the outlet vent 812 on the elbow connector. The mouthpiece with nose flap has the advantage of overcoming any leakages that may occur through the nose, when no flap or blockage is provided with a mouthpiece. Therefore, drying of the airway passages and loss of pressure of the gases is reduced.

Figure 9B:
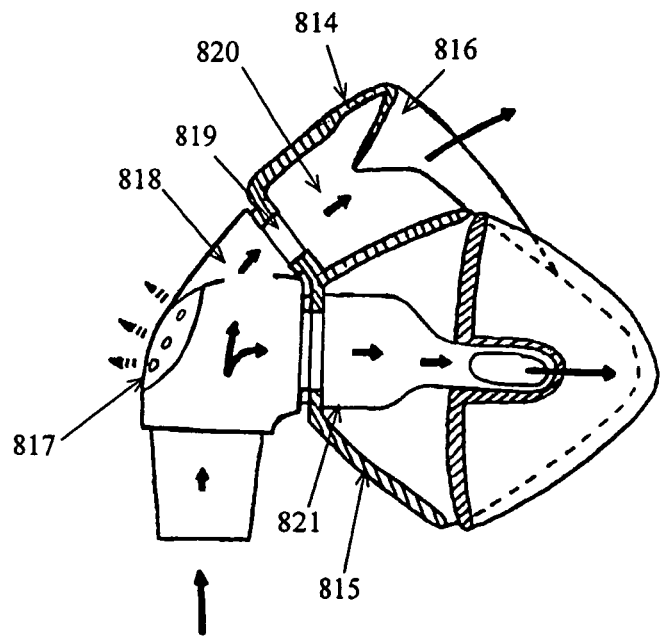
FIG. 9B is a cross sectional view of another form of a mouthpiece that has a nose flap and nasal cannula.

A further embodiment of a mouthpiece is shown in FIG. 9B. Here the mouthpiece 813 has a similar nose flap 814 to that described with reference to FIG. 9A, but the passages to each of the nose and mouth cavities is separate not combined as in FIG. 9A. The nose flap 814 is preferably moulded with a complete outer flap 815 and has a flange or lip 816 about its edge to assist with sealing of the nose flap 814 about the patient's nose. The elbow connector 817 has an extension part 818 that fits to an inlet 819 of the nose flap 814 so that gases are directed to the passageway 820 formed inside the nose flap 814, but gases are also directed into the tubular passageway 821 in the usual manner.

Figure 9C:
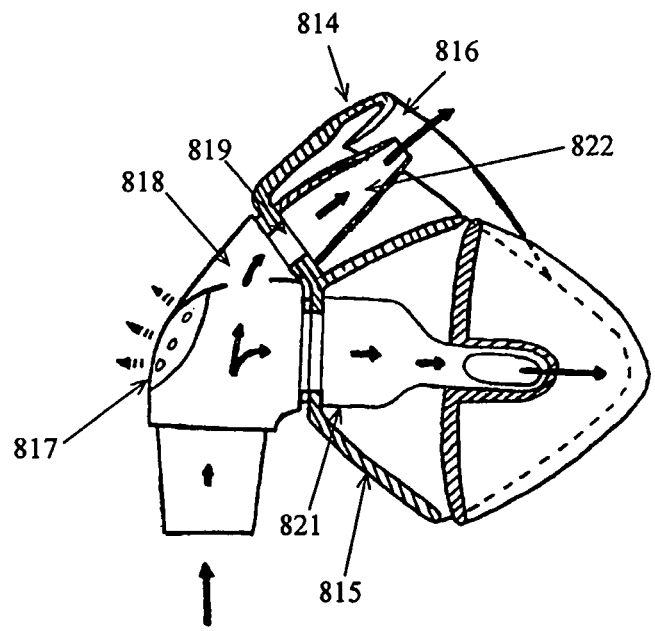
FIG. 9C is a cross sectional view of yet another form of a mouthpiece that has a nose flap and nasal cannula.

Another embodiment of a mouthpiece is shown in FIG. 9C. Here the mouthpiece is identical to that of FIG. 9C, but has additional nasal cannula 822 attached to the inlet 819 to the nose flap 814. The nasal cannula 822 (of which only one of a pair is shown) in use would extend into the patient's nares. The cannula 822 would assist in directing gases into the nasal cavities and also reduce leakage of gases. Also, with this mouthpiece a patient using the mouthpiece will have the option to breathe nasally or orally.

Figure 9D:
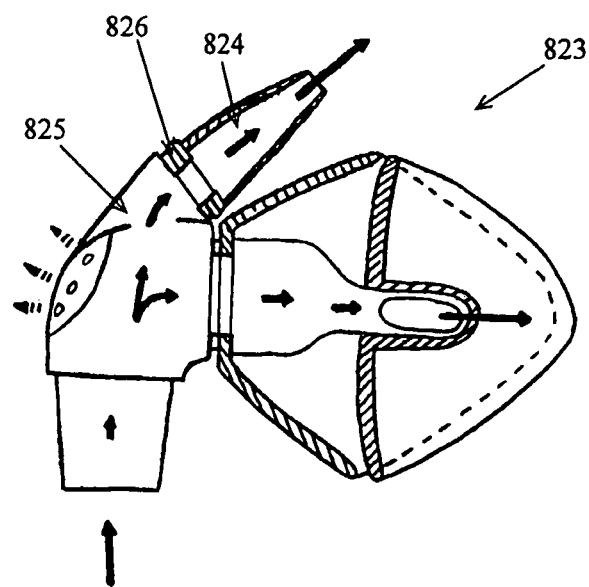
FIG. 9D is a cross sectional view of a further form of a mouthpiece that has nasal cannula extending from it.

Yet another embodiment of a mouthpiece is shown in FIG. 9D. The mouthpiece 823 is very similar to that of FIG. 9C but has no nose flap. Here the nasal cannula 824 provide for sealing in the nares and prevent leakage. The connection between the connector 825 and the cannula may have an extension mechanism, such as bellow like corrugations 826 formed in the plastics material that the cannula 824 are formed from. The bellows allow the cannula to be adjusted in length and always provide a force toward the nose because of the mechanical and geometrical properties of the bellows in the silicone, so that they can be fitted to different sized and shaped patients. Also, the bellows would enable the cannula 824 to be moved or adjusted to better fit particular patients and assist user comfort. In the preferred form of the mouthpiece different sizes of cannula may be provided with the mouthpiece. The cannula can therefore be detached and different sized cannula fitted to allow fitting of the mouthpiece and cannula to fit different shaped noses. In the preferred form the cannula are made from a soft material, such as silicone.

Finally, FIG. 10 shows an outer flap 827 for a mouthpiece 828 having protrusions 828, 829 extending out from the upper edge 830 of the outer flap 827. The protrusions would in use rest against the outer regions of a patients nose and press the outer edges of the nose inwards to partially or fully block the patient's nares. This would also have the effect of preventing leakage from the patient's nares. The protrusions are preferably made from a soft material such as silicone.

This flap 827 may be used with any of the mouthpieces previously described except for the mouthpieces having the nasal cannula or nasal flap.

In other forms of the mouthpiece a nose flap or blocked cannula may be provided to seal and prevent breathing through the nose by either blocking the nose by applying pressure on the outside of the nose to force the nares closed, squeezing the sides of the user's nose, covering the user's nares or in the case of a cannula, by being inserted into the user's nose.

Mouth Cavity Proper Shield

Two alternative embodiments of the mouthpiece will now be described, with particular reference to FIGS. 23 and 24. Both alternative embodiments feature a paired shield or flap arrangement, similar to that already described for the outer flap and vestibular shield pairing.

Figure 23:
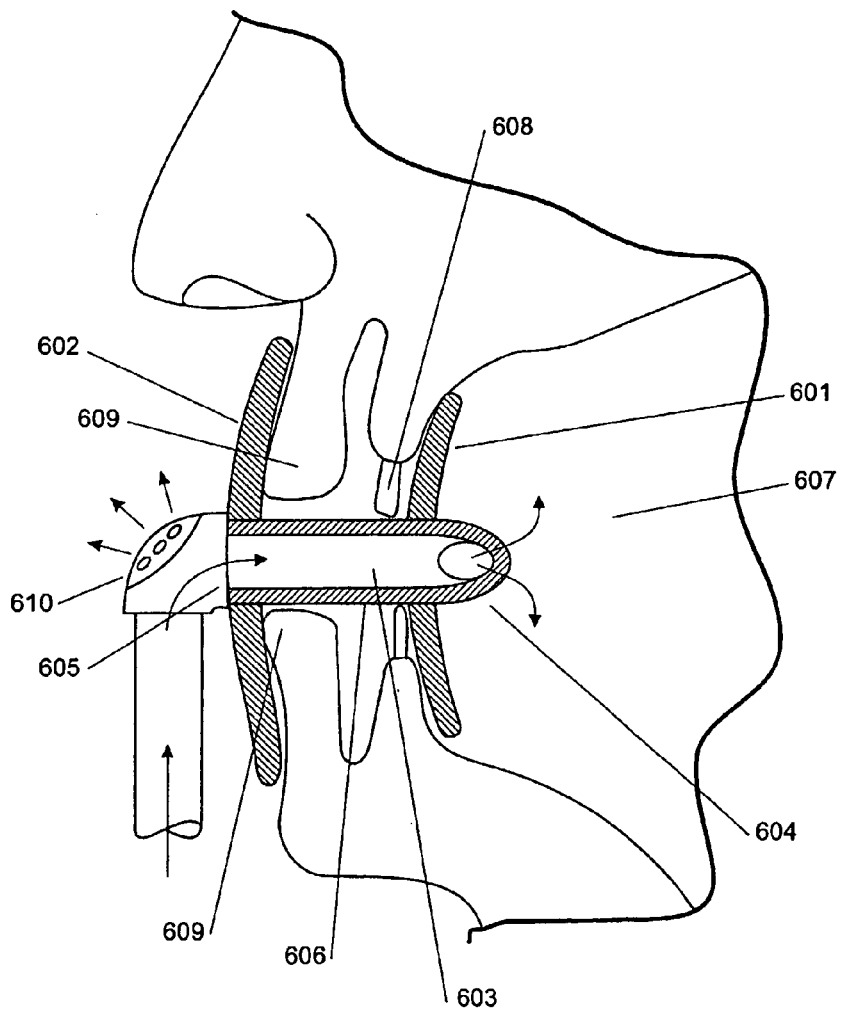
FIG. 23 is a cutaway view of an alternative embodiment of the mouthpiece with an outer flap in use, and an inner shield in the mouth cavity proper, behind the teeth, with an outlet valve mounted on the elbow joint

In the first alternative embodiment, as shown in FIG. 23, vestibular shield 21 of FIG. 4 is replaced by a shield 601, located in the mouth cavity proper 607 (hereto forward referred to as the MCP shield 601), which is paired with an outer flap 602. The MCP shield 601 is designed to sit in the mouth cavity proper, between the teeth and the tongue. In all other respects, it fulfils the same gas diffusion and sealing functions as have already been outlined for the different embodiments of the vestibular shield.

In this preferred embodiment, the MCP shield 601 is a generally flat and generally rectangularly-shaped member in front elevation having a curved profile that reflects the curvature of a user's jaw and in turn the curvature of the mouth cavity region. A gases passageway 603 extends through the mouthpiece and has an outlet 604 exiting through the MCP shield 601. The outlet 604 can be configured so that the gases are diffused in a similar manner to that already described, or the MCP shield 601 may be fitted with a plurality of ventilation apertures as already described for the vestibular shield. The mouthpiece 1 also has an outer flap 602 similar to that already described. The inlet 605 and connector 606 are also similar to the embodiments already described.

The MCP shield 601 is preferably formed in a soft and supple material such as silicon. The connector 606 between the outer flap 602 and MCP shield 601, and outlet part 604 are made of a stiffer material, such as a hard plastics material, for example, polycarbonate, in order to prevent an inadvertent squeezing or pinching closed of the connector 606 by the teeth 608 or lips 609 of the user if the user unconsciously attempts to close their mouth during sleep.

Figure 24:
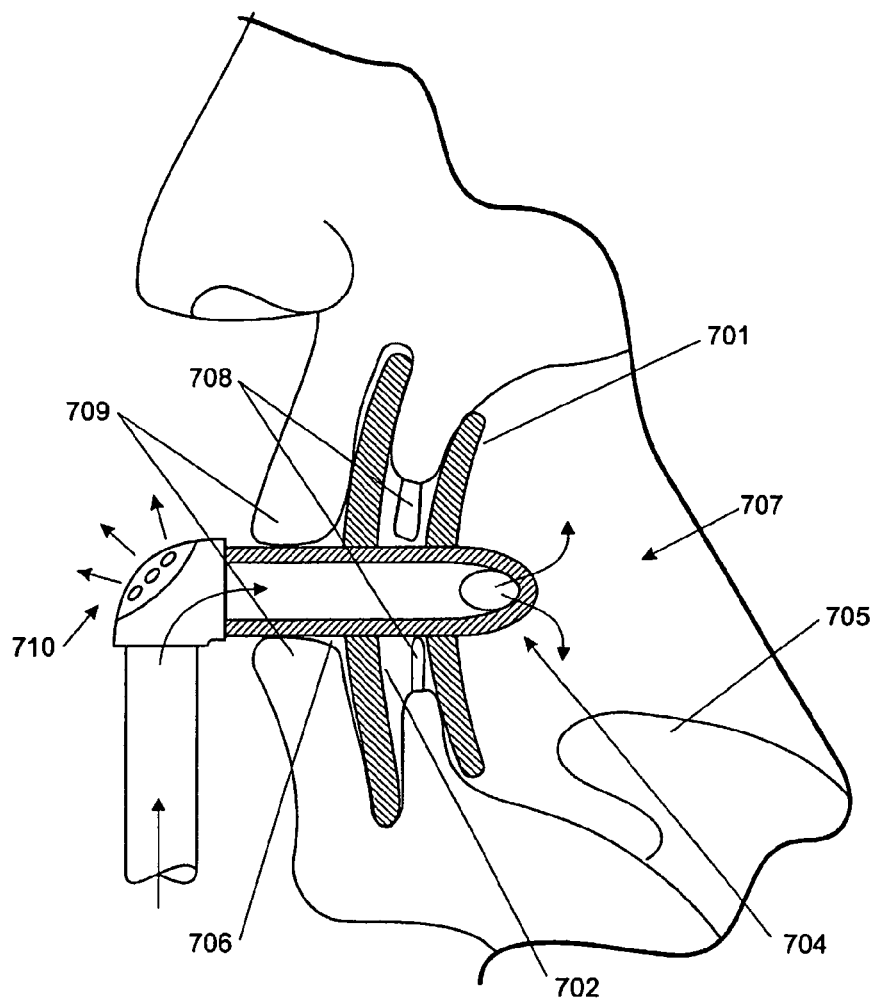
FIG. 24 is a cutaway view of an alternative embodiment of the mouthpiece with a shield in the mouth cavity proper and a vestibular shield, with an outlet valve mounted on the elbow joint, and no extra-oral sealing means.

In the second alternative embodiment, as shown in FIG. 24, the mouthpiece 1 consists of a vestibule guard 702, paired with a shield 701 located in the mouth cavity proper 707 (hereto forward referred to as the MCP shield 701), and a connector 706 with outlet 704. There is no outer flap in this embodiment. The vestibular guard 702 in this embodiment contains no gases diff-using means, or apertures or channels, and is preferably formed in a soft and supple material such as silicon. The MCP shield 701 is designed to sit in the mouth cavity proper, between the teeth 708 and the tongue 705, and fulfils the same gas diffusion and sealing functions as have been outlined for the vestibular guard 21 of FIG. 4 in the preferred embodiment. The connector 706 is made of a stiffer material, such as a hard plastics material, for example, polycarbonate, in order to prevent an inadvertent squeezing or pinching closed of the connector 706 by the teeth 708 or lips 709 of the user if the user unconsciously attempts to close their mouth during sleep.

In both of the alternative embodiments described above, the mouthpiece 1 can include an adjusting means such as the bellows extension previously described and shown in FIGS. 18 and 19, and a connection to the breathing circuit via an elbow connector as already described. In the embodiments shown, the elbow connector includes an outlet valve, shown as component 610 in FIG. 23 and component 710 in FIG. 24. In alternative embodiments, the outlet valve may be replaced by either of the alternative gas diffusion arrangements as already described. Also, in the embodiment shown in FIG. 23, a nose flap as previously described may be included.

Advantages

From the above it can be seen that the present invention provides a system including a mouthpiece for oral delivery of CPAP treatment which once is low cost and effective. Unlike other mouthpieces the mouthpiece of the present invention does not require custom orthodontic fitting, as the mouthpiece does not rely on accurate alignment with the user's teeth or the user's palate to provide location and retention within the user's mouth. In the preferred embodiment the mouthpiece resides in the vestibule between the teeth and lips and the teeth and cheeks, and the lateral and vertical extension of a vestibular shield requires that the user's lips be actively manipulated for the vestibular shield to be removed. Furthermore the vestibular shield is provided with an outlet that allows for diffusion of the gases provided to the user and thus the mouthpiece does not require any tongue depressor. The mouthpiece and vestibular shield thus prevent a user blocking the flow of gases from the mouthpiece, yet is more comfortable for the user than prior art devices. With the addition of the extra-oral flap the mouthpiece and associated tubing is held securely in place without the need for external strapping, and an effective seal is created around the user's mouth.

Similar advantages are conferred by the alternative embodiments outlined, where the paired shield arrangements are located either extra-orally and in the mouth cavity proper, or as a paired vestibular shield and mouth cavity proper shield. In both of these alternative embodiments, accurate location and retention in a user's mouth is achieved, requiring a conscious effort by the user to remove the mouthpiece. In both of these embodiments, an outlet that allows for diffusion of the gases is provided that does not require any tongue depressor and the paired shield arrangement ensures that the airflow will occur substantially through the gases passageway, with little leakage.

We claim:

1. A patient interface for the delivery of gases from a source to a user, comprising:
    an elbow connector capable of receiving gases from the source;
    an outer flap adapted to conform to a mouth of the user and in fluid connection with said elbow connector, said outer flap configured to apply a compressive force around the user's mouth when worn, said outer flap configured to define a gases space around the user's mouth and capable of delivering said gases from said elbow connector to an oral passage of the user;
    a tubular passageway extending through said outer flap to an outlet part, the tubular passageway in fluid communication with said elbow connector to deliver gases from said elbow connector to the user's mouth;
    the outlet part comprising two oppositely curved arms projecting away from the outer flap and adapted to extend into the user's mouth, each of the arms comprising an outlet such that the outlet part comprises two opposite outlets adapted to direct gases flow around sides of the user's mouth as gases flow out of said tubular passageway and into the user's mouth, wherein the two arms are two tubular spaced arms adapted to extend toward opposite sides of the user's mouth and having the opposite outlets adapted to direct gases to the opposite sides of the user's mouth; and
    a nasal cannula configured to seal in each nare of the user, said nasal cannula attached to and in fluid connection with one of said outer flap and said elbow connector such that said nasal cannula is capable of delivering said gases to the user's nares.

2. A patient interface according to claim 1 wherein said elbow connector is substantially L-shaped, where one end of the L-shaped elbow connector is connected in use to said nasal cannula and said outer flap, while another end of the L-shaped nasal connector is adapted to receive said gases for delivery to the user.

3. A patient interface as claimed in claim 2 wherein said elbow connector comprises a plurality of apertures in an apex of the L-shape of said elbow connector, said apertures adapted to vent gases exhaled from the user.

4. A patient interface as claimed in claim 1 wherein said elbow connector having an outlet vent to allow diffusion of exhaled gases from the user.

5. A patient interface as claimed in claim 1 wherein said nasal cannula includes an extension mechanism, said extension mechanism adapted to allow said nasal cannula to adjustably extend from said elbow connector or said outer flap.

6. A patient interface as claimed in claim 5 wherein said extension mechanism is a series of bellow-like corrugations in said nasal cannula allowing a length of said nasal cannula to be adjusted.

7. A patient interface as claimed in claim 1 wherein said nasal cannula comprises a pair of nasal prongs.

8. A patient interface as claimed in claim 1 wherein said nasal cannula is capable of detaching from one of said elbow connector and said outer flap, allowing different sized nasal cannulas to be connected to one of said elbow connector and said outer flap.

9. A patient interface as claimed in claim 1 wherein said nasal cannula is made of silicone.

10. A patient interface as claimed in claim 1 wherein said outer flap has a lip extending around its perimeter to assist in sealing of said outer flap against the user's face.

11. A patient interface as claimed in claim 1 wherein said outer flap is made from silicon.

12. A patient interface as claimed in claim 1 further including a vestibular shield connected to said tubular passageway, said vestibular shield being disposed in use within a user's mouth vestibule.

13. A patient interface according to claim 1, wherein said outer flap comprises an edge, said edge applying said compressive force around the user's mouth when worn.

14. A patient interface according to claim 1, further comprising an adjustment mechanism that allows the user to adjust the compressive force applied to the user's mouth when worn by adjusting a distance between the elbow connector and the outer flap.

15. A patient interface according to claim 14, wherein said adjustment mechanism comprises a sliding sleeve.

16. A patient interface according to claim 1, further comprising at least one outlet vent in fluid communication with said elbow connector to allow diffusion of exhaled gases from the user.

17. A patient interface according to claim 1, further comprising a vestibular shield configured to be inserted between lips and gums of the user during use, wherein a distance between the outer flap and the vestibular shield is adjustable to apply sufficient compressive force around the user's lips to maintain the outer flap in contact with the user while the user sleeps.

18. A patient interface according to claim 1, wherein said outer flap further comprises at least one outlet in fluid communication with said elbow connector and configured to deliver said gasses to the user's oral passage, said outlet having an elongated oval shape extending towards lateral sides of said outer flap.

19. A patient interface for the delivery of gases from a source to a user, comprising:
   an elbow connector capable of receiving gases from the source;
   an outer flap adapted to conform to a mouth of the user and in fluid connection with said elbow connector, said outer flap configured to apply a compressive force about an outside of the user's mouth when worn, said outer flap configured to deliver said gases from said elbow connector to an oral passage of the user;
   a tubular passageway in fluid communication with said elbow connector and extending through said outer flap to an outlet part, the outlet part in fluid communication with said tubular passageway and comprising two tubular, oppositely curved arms projecting away from said outer flap and configured to extend toward opposite sides of the user's mouth, each of the arms comprising an outlet such that the outlet part comprises two opposite outlets adapted to direct gases flow around the sides of the user's mouth to opposite sides of the user's mouth as gases flow out of said tubular passageway and into the user's mouth;
   a nasal cannula configured to seal in each nare of the user, said nasal cannula attached to and in fluid connection with one of said outer flap and said elbow connector such that said nasal cannula is capable of delivering said gases to the user's nares; and
   a nasal cannula extension mechanism adapted to allow said nasal cannula to adjustably extend from at least one of said elbow connector and said outer flap.

20. A patient interface as claimed in claim 19 wherein said nasal cannula extension mechanism is bellow-like corrugations in said nasal cannula allowing a length of said nasal cannula to be adjusted.

21. A patient interface as claimed in claim 19 wherein said nasal cannula is capable of being detached from one of said elbow connector and said outer flap, allowing for different sized nasal cannulas to be attached to one of said elbow connector and said outer flap.

22. A patient interface for the delivery of gases from a source to a user, comprising:
   an elbow connector capable of receiving gases from the source;
   an outer flap adapted to conform to a mouth of the user and in fluid connection with said elbow connector, said outer flap configured to provide a substantial seal about an outside of the user's mouth and capable of delivering said gases from said elbow connector to an oral passage of the user;
   a tubular passageway in fluid communication with said elbow connector and extending through said outer flap;
   an outlet part in fluid communication with said tubular passageway and comprising two arms projecting away from said outer flap and configured to be disposed in the user's mouth, wherein the two arms are tubular and oppositely curved and configured to extend toward opposite sides of the user's mouth, each of said arms including an outlet such that the outlet part comprises two opposite outlets configured to direct gases to opposite sides of the user's mouth;
   a nasal cannula configured to seal in each nare of the user, said nasal cannula attached to and in fluid connection with one of said outer flap and said elbow connector such that said nasal cannula is capable of delivering said gases to the user's nares; and
   an outlet vent in fluid communication with said elbow connector to allow diffusion of exhaled gases from the user.

23. A patient interface for the delivery of gases from a source to a user, comprising:
   an elbow connector capable of receiving gases from the source;
   an outer flap adapted to conform to a mouth of the user and in fluid connection with said elbow connector, said outer flap configured to apply a compressive force around the user's mouth when worn, said outer flap configured to define a gases space around the user's mouth and capable of delivering said gases from said elbow connector to an oral passage of the user;
   a connector coupled to said outer flap and in fluid communication with said elbow connector;
   a substantially tubular U-shaped outlet part coupled to the connector and comprising two oppositely curved arms, each arm having an outlet such that the outlet part comprises two opposite outlets, the outlet part configured to be disposed in the user's mouth in use; and
   a nasal cannula configured to seal in each nare of the user, said nasal cannula attachable to and detachable from and in fluid connection with at least one of said outer flap and said elbow connector such that said nasal cannula is capable of delivering said gases to the user's nares and such that different sized nasal cannula can be connected to one of said elbow connector and said outer flap.

24. A system for delivery of gases to a user, said system comprising:
   a gases source;
   a breathing circuit defining a gases pathway, said breathing circuit connected to and in fluid communication with the gases source; and
   a patient interface connected to and in fluid communication with said breathing circuit to receive said gases from said gases source through said breathing circuit, said patient interface comprising:
   an elbow connector capable of receiving gases from the source,
   an outer flap configured to fit around and enclose a mouth of the user such that said outer flap is configured to apply a compressive force around the user's mouth when worn, said outer flap in fluid connection with said elbow connector, said outer flap configured to define a gases space around the user's mouth and capable of delivering said gases from said elbow connector to an oral passage of the user,
   a connector coupled to said outer flap and in fluid communication with said elbow connector;
   an outlet part coupled to the connector and comprising two tubular and oppositely curved arms configured to extend into the user's mouth toward opposite sides of the user's mouth, each of the arms comprising an outlet such that the outlet part comprises two opposite outlets configured to direct gases toward opposite sides of the user's mouth; and
   a nasal cannula configured to seal in each nare of said user, said cannula attached to and in fluid connection with one of said outer flap and said elbow connector such that said nasal cannula is capable of delivering said gases to the user's nares.

* * * * *